(12) United States Patent
Simiele et al.

(10) Patent No.: US 11,944,737 B2
(45) Date of Patent: Apr. 2, 2024

(54) AIR VENTING METER LID ADAPTER

(71) Applicant: C. R. Bard, Inc., Franklin Lakes, NJ (US)

(72) Inventors: David M. Simiele, Roswell, GA (US); Jason Jishen Cheng, Avondale Estates, GA (US)

(73) Assignee: C. R. Bard, Inc., Franklin Lakes, NJ (US)

( * ) Notice: Subject to any disclaimer, the term of this patent is extended or adjusted under 35 U.S.C. 154(b) by 0 days.

(21) Appl. No.: 17/532,454

(22) Filed: Nov. 22, 2021

(65) Prior Publication Data

US 2022/0160949 A1 May 26, 2022

Related U.S. Application Data

(60) Provisional application No. 63/117,906, filed on Nov. 24, 2020.

(51) Int. Cl.
*A61M 1/00* (2006.01)
(52) U.S. Cl.
CPC .............. *A61M 1/60* (2021.05); *A61M 1/86* (2021.05); *A61M 2202/0496* (2013.01)
(58) Field of Classification Search
CPC .......... A61M 1/60; A61M 1/604; A61M 1/86; A61M 39/1055; A61M 2202/0496; A61M 1/69; A61M 1/70; A61M 1/75; A61M 1/741; A61M 1/64; A61F 5/4405; A61F 5/441; A61F 2005/4415
See application file for complete search history.

(56) References Cited

U.S. PATENT DOCUMENTS

| | | |
|---|---|---|
| 3,114,916 A | 12/1963 | Hadley |
| 3,583,401 A | 6/1971 | Vailiancourt et al. |

(Continued)

FOREIGN PATENT DOCUMENTS

| | | | | |
|---|---|---|---|---|
| EP | 1872752 A1 | 1/2008 | | |
| EP | 2730299 A1 * | 5/2014 | .......... | A61M 1/0001 |

(Continued)

OTHER PUBLICATIONS

PCT/US2020/066707 filed Dec. 22, 2020 International Search Report and Written Opinion dated Apr. 15, 2021.

(Continued)

*Primary Examiner* — Catharine L Anderson
*Assistant Examiner* — Arjuna P Chatrathi
(74) *Attorney, Agent, or Firm* — Rutan & Tucker LLP

(57) ABSTRACT

A lid adapter for coupling with a lid of a collection container where the lid includes an outlet vent. The lid adapter including a housing including a top surface and one or more side panels that are configured to couple with a top of the lid and a port coupled to the top surface and configured to rotate between a first position and a second position, wherein when the lid adapter is coupled to the lid and the port is in the first position, a fluid seal is established between a distal end of the port and the top of the lid surrounding the outlet vent thereby enabling fluid flow from the outlet vent and through the port. When the port is in the second position, the fluid seal is not established, and when the port is in the first position, the port is disposed perpendicularly to the top surface.

22 Claims, 9 Drawing Sheets

(56) References Cited

U.S. PATENT DOCUMENTS

| | | | |
|---|---|---|---|
| 3,598,124 A | 8/1971 | Andersen et al. | |
| 3,661,143 A | 5/1972 | Henkin | |
| 3,861,394 A | 1/1975 | Villari | |
| 3,901,235 A | 8/1975 | Patel et al. | |
| 3,955,574 A | 5/1976 | Rubinstein | |
| 4,084,593 A | 4/1978 | Jarund | |
| 4,265,243 A | 5/1981 | Taylor | |
| 4,305,403 A | 12/1981 | Dunn | |
| 4,315,506 A | 2/1982 | Kayser et al. | |
| 4,360,933 A | 11/1982 | Kimura et al. | |
| 4,465,485 A * | 8/1984 | Kashmer | A61M 1/784 604/320 |
| 4,531,939 A | 7/1985 | Izumi | |
| 4,631,061 A | 12/1986 | Martin | |
| 4,654,029 A | 3/1987 | D'Antonio | |
| 4,747,166 A | 5/1988 | Kuntz | |
| 4,819,684 A | 4/1989 | Zaugg et al. | |
| 4,872,579 A | 10/1989 | Palmer | |
| 4,990,137 A | 2/1991 | Graham | |
| 5,002,528 A | 3/1991 | Palestrant | |
| 5,071,411 A | 12/1991 | Hillstead | |
| 5,186,431 A | 2/1993 | Tamari | |
| 5,318,550 A | 6/1994 | Cermak et al. | |
| 5,405,319 A | 4/1995 | Abell et al. | |
| 5,738,656 A | 4/1998 | Wagner et al. | |
| 5,894,608 A | 4/1999 | Birbara | |
| 6,007,521 A | 12/1999 | Bidwell et al. | |
| 6,106,506 A | 8/2000 | Abell et al. | |
| 6,183,454 B1 | 2/2001 | Levine et al. | |
| 8,337,475 B2 | 12/2012 | Christensen et al. | |
| 8,512,301 B2 | 8/2013 | Ma | |
| 10,391,275 B2 | 8/2019 | Burnett et al. | |
| 10,426,919 B2 | 10/2019 | Erbey, II et al. | |
| 10,506,965 B2 | 12/2019 | Cooper et al. | |
| 10,737,057 B1 | 8/2020 | Mikhail et al. | |
| 10,772,998 B2 | 9/2020 | Luxon et al. | |
| 2002/0000253 A1 | 1/2002 | Fillmore et al. | |
| 2002/0161317 A1 | 10/2002 | Risk et al. | |
| 2003/0078638 A1 | 4/2003 | Voorhees et al. | |
| 2004/0176746 A1 | 9/2004 | Forral | |
| 2004/0230181 A1 | 11/2004 | Cawood | |
| 2004/0236292 A1 | 11/2004 | Tazoe et al. | |
| 2004/0254547 A1 | 12/2004 | Okabe et al. | |
| 2005/0209585 A1 | 9/2005 | Nord et al. | |
| 2005/0245898 A1* | 11/2005 | Wright | A61M 1/86 604/533 |
| 2005/0261619 A1 | 11/2005 | Gay | |
| 2006/0015190 A1 | 1/2006 | Robertson | |
| 2006/0079854 A1 | 4/2006 | Kay et al. | |
| 2006/0155260 A1 | 7/2006 | Blott et al. | |
| 2006/0235353 A1 | 10/2006 | Gelfand et al. | |
| 2006/0271019 A1 | 11/2006 | Stoller et al. | |
| 2007/0078444 A1 | 4/2007 | Larsson | |
| 2007/0142729 A1 | 6/2007 | Pfeiffer et al. | |
| 2007/0272311 A1 | 11/2007 | Trocki et al. | |
| 2008/0156092 A1 | 7/2008 | Boiarski | |
| 2009/0157016 A1 | 6/2009 | Adahan | |
| 2009/0157040 A1 | 6/2009 | Jacobson et al. | |
| 2009/0326483 A1 | 12/2009 | Green | |
| 2010/0106116 A1* | 4/2010 | Simmons | A61M 1/60 604/319 |
| 2010/0130949 A1* | 5/2010 | Garcia | A61M 25/0017 604/326 |
| 2011/0060300 A1 | 3/2011 | Weig et al. | |
| 2012/0323144 A1 | 12/2012 | Coston et al. | |
| 2013/0218106 A1* | 8/2013 | Coston | A61M 1/00 604/317 |
| 2014/0200558 A1 | 7/2014 | McDaniel | |
| 2015/0126975 A1 | 5/2015 | Wuthier | |
| 2015/0290448 A1* | 10/2015 | Pavlik | A61J 1/201 604/533 |
| 2016/0135982 A1 | 5/2016 | Garcia | |
| 2016/0183819 A1 | 6/2016 | Burnett et al. | |
| 2016/0310711 A1 | 10/2016 | Luxon et al. | |
| 2017/0072125 A1 | 3/2017 | Wallenås et al. | |
| 2017/0136209 A1 | 5/2017 | Burnett et al. | |
| 2017/0143566 A1 | 5/2017 | Elku et al. | |
| 2017/0241978 A1 | 8/2017 | Duval | |
| 2017/0312114 A1 | 11/2017 | Glithero | |
| 2018/0015251 A1 | 1/2018 | Lampotang et al. | |
| 2018/0071441 A1 | 3/2018 | Croteau et al. | |
| 2018/0104391 A1 | 4/2018 | Luxon et al. | |
| 2018/0110456 A1 | 4/2018 | Cooper et al. | |
| 2018/0125697 A1 | 5/2018 | Ferrera | |
| 2018/0177458 A1 | 6/2018 | Burnett et al. | |
| 2018/0235523 A1 | 8/2018 | Sauder | |
| 2018/0245699 A1 | 8/2018 | Lee | |
| 2018/0360424 A1 | 12/2018 | Yurek et al. | |
| 2019/0009021 A1 | 1/2019 | Nelson et al. | |
| 2019/0038451 A1 | 2/2019 | Harvie | |
| 2019/0046102 A1 | 2/2019 | Kushnir et al. | |
| 2019/0126006 A1 | 5/2019 | Rehm et al. | |
| 2019/0143094 A1 | 5/2019 | DeMeritt | |
| 2019/0151610 A1 | 5/2019 | Fletter | |
| 2019/0343445 A1 | 11/2019 | Burnett et al. | |
| 2020/0000979 A1* | 1/2020 | Myers | A61M 39/24 |
| 2020/0061281 A1 | 2/2020 | Desouza et al. | |
| 2020/0315837 A1* | 10/2020 | Radl | A61M 1/74 |
| 2021/0077207 A1 | 3/2021 | Jouret et al. | |
| 2022/0152345 A1 | 5/2022 | Simiele et al. | |
| 2022/0176031 A1 | 6/2022 | Cheng et al. | |
| 2022/0193366 A1 | 6/2022 | Cheng et al. | |
| 2022/0218890 A1 | 7/2022 | Chavan | |
| 2022/0218973 A1 | 7/2022 | Chavan et al. | |
| 2022/0218974 A1 | 7/2022 | Chavan et al. | |
| 2022/0273213 A1 | 9/2022 | Sokolov et al. | |
| 2022/0305189 A1 | 9/2022 | Chavan et al. | |
| 2022/0330867 A1 | 10/2022 | Conley et al. | |
| 2022/0362080 A1 | 11/2022 | McCorquodale et al. | |
| 2022/0409421 A1 | 12/2022 | Hughett et al. | |
| 2023/0013353 A1 | 1/2023 | Chavan et al. | |
| 2023/0030637 A1 | 2/2023 | Gloeckner et al. | |
| 2023/0054937 A1 | 2/2023 | Chancy et al. | |
| 2023/0083906 A1 | 3/2023 | Jones et al. | |
| 2023/0310837 A1 | 10/2023 | Gamsizlar et al. | |

FOREIGN PATENT DOCUMENTS

| | | |
|---|---|---|
| WO | 2009026237 A1 | 2/2009 |
| WO | 2012016179 A1 | 2/2012 |
| WO | 2015019056 A1 | 2/2015 |
| WO | 2015105916 A1 | 7/2015 |
| WO | 2016012494 A1 | 1/2016 |
| WO | 2017177068 A1 | 10/2017 |
| WO | 2018136306 A1 | 7/2018 |
| WO | 2018191193 A1 | 10/2018 |
| WO | 2019004854 A1 | 1/2019 |
| WO | 2020033752 A1 | 2/2020 |
| WO | 2022/159333 A1 | 7/2022 |
| WO | 2022251425 A1 | 12/2022 |
| WO | 2023086394 A1 | 5/2023 |

OTHER PUBLICATIONS

U.S. Appl. No. 17/526,994, filed Nov. 15, 2021 Restriction Requirement dated Jan. 3, 2023.
U.S. Appl. No. 17/556,942, filed Dec. 20, 2021 Non-Final Office Action dated Jan. 31, 2023.
PCT/US2022/012373 filed Jan. 13, 2022 International Search Report and Written Opinion dated Apr. 19, 2022.
PCT/US2022/049418 filed Nov. 9, 2022 International Search Report and Written Opinion dated Feb. 10, 2023.
U.S. Appl. No. 17/526,994, filed Nov. 15, 2021 Non-Final Office Action dated May 10, 2023.
U.S. Appl. No. 17/561,504, filed Dec. 23, 2021 Non-Final Office Action dated Mar. 14, 2023.
U.S. Appl. No. 17/902,705, filed Sep. 2, 2022 Non-Final Office Action dated May 24, 2023.
U.S. Appl. No. 17/542,060, filed Dec. 3, 2021 Non-Final Office Action dated Jun. 27, 2023.

(56) References Cited

OTHER PUBLICATIONS

U.S. Appl. No. 17/556,942, filed Dec. 20, 2021 Advisory Action dated Sep. 1, 2023.
U.S. Appl. No. 17/556,942, filed Dec. 20, 2021 Final Office Action dated Jul. 12, 2023.
U.S. Appl. No. 17/561,458, filed Dec. 23, 2021 Non-Final Office Action dated Jun. 16, 2023.
U.S. Appl. No. 17/561,504, filed Dec. 23, 2021 Final Office Action dated Jul. 19, 2023.
U.S. Appl. No. 17/863,898, filed Jul. 13, 2022 Non-Final Office Action dated Jul. 17, 2023.
U.S. Appl. No. 17/902,705, filed Sep. 2, 2022 Final Office Action dated Aug. 17, 2023.
U.S. Appl. No. 17/373,568, filed Jul. 12, 2021 Non-Final Office Action dated Nov. 9, 2023.
U.S. Appl. No. 17/526,994, filed Nov. 15, 2021 Final Office Action dated Oct. 24, 2023.
U.S. Appl. No. 17/542,060, filed Dec. 3, 2021 Non-Final Office Action dated Nov. 28, 2023.
U.S. Appl. No. 17/556,942, filed Dec. 20, 2021 Non-Final Office Action dated Nov. 3, 2023.
U.S. Appl. No. 17/561,458, filed Dec. 23, 2021 Final Office Action dated Sep. 12, 2023.
U.S. Appl. No. 17/561,458, filed Dec. 23, 2021 Notice of Allowance dated Dec. 6, 2023.
U.S. Appl. No. 17/561,504, filed Dec. 23, 2021 Non-Final Office Action dated Nov. 27, 2023.
U.S. Appl. No. 17/863,898, filed Jul. 13, 2022 Final Office Action dated Nov. 22, 2023.
U.S. Appl. No. 17/902,705, filed Sep. 2, 2022 Advisory Action dated Oct. 19, 2023.
U.S. Appl. No. 17/902,705, filed Sep. 2, 2022 Non-Final Office Action dated Dec. 7, 2023.

* cited by examiner

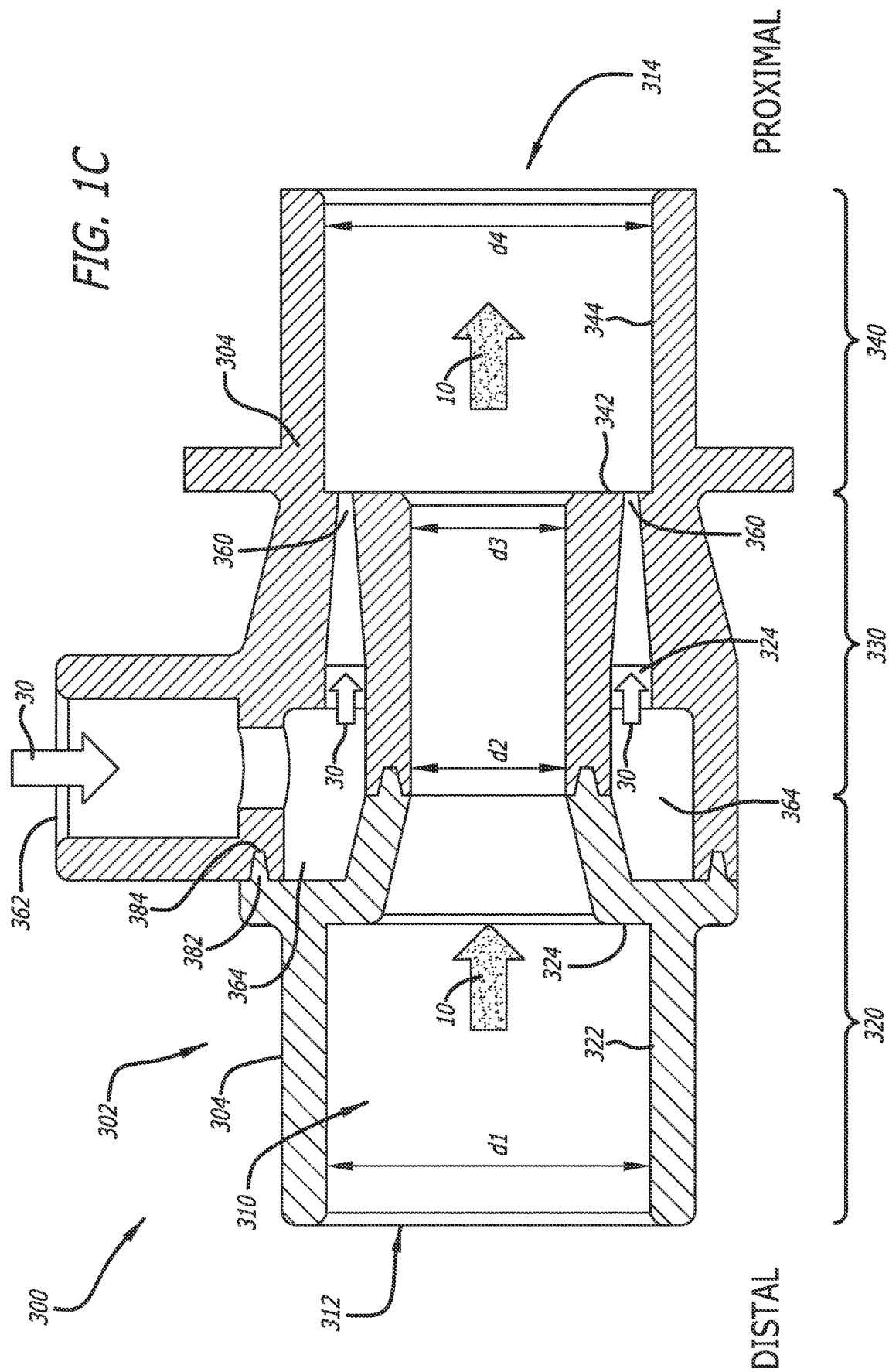

AIR VENTING METER LID ADAPTER

PRIORITY

This application claims the benefit of priority to U.S. Provisional Application No. 63/117,906, filed Nov. 24, 2020, which is incorporated by reference in its entirety into this application.

BACKGROUND

Briefly summarized, systems and methods disclosed herein are directed to a fluid drainage system including an adapter for providing airflow to remove fluid within drainage tubing. A fluid collection system for use with a patient may utilize a catheter to drain fluid (e.g., urine) from the patient, which is transferred through a drainage tube to a collection container. In use, columnized fluid may form within the catheter lumen or drainage tube. In particular, columnized drainage fluid (e.g., a drainage fluid which fills a drainage lumen, or a pooled fluid), may lead to back-pressure against a bladder, causing inaccurate fluid measurements over time. For example, dependent loops of columnized urine may form within drainage tubing associated with catheters. Moreover, urine pooling within a drainage tube can become a source of catheter associated urinary tract infection ("CAUTI") causing agents such as bacteria, microbes, and the like. Hospital Acquired Infections ("HAI"), such as CAUTI, are detrimental to the patient, and also incur extra costs in treating these additional complications. Fluid should therefore be returned to the collection container for accurate measurements. As used herein, a dependent loop may be any portion of the drainage tube that is lower than a downstream portion so as to create a positive incline relative to the direction of fluid flow. Dependent loops can form in slack portions of the drainage tube. The dependent loop may be a complete loop, a partial loop, or any segment of drainage tubing that causes fluid to pool in the drainage tubing.

Current technology may utilize a low flow-rate of air to transport the fluid (urine) trapped in the drainage tube (e.g., in a dependent loop or otherwise residually attached to the drainage tube wall) toward the drainage bag, i.e., disposed within a collection container. However, as has been found, the low flow-rate of air is often insufficient to transport all or substantially all of the trapped fluid to the drainage bag, which leaves an amount of fluid within the drainage tubing.

When a high flow-rate of air is used to transport the trapped fluid, the bag undesirably inflates. Some drainage bags may include vent ports to passively expel air, but these vents do not operate at a high enough flow-rate to keep the drainage bag from inflating.

Thus, what is needed are devices, systems and methods thereof for adapting existing passive vents of fluid drainage bags with a suction line to assist fluid removal.

SUMMARY

One problem that may arise during fluid drainage from human bodies is the formation of columnized fluid in tubing. The removal of this fluid using air may cause a build-up of air in storage collection bags.

Briefly summarized, embodiments disclosed herein are directed to systems, methods and apparatuses for adapters for removing gas using suction.

In some embodiments, a fluid drainage system comprises a catheter; a collection container comprising a vent to allow gas to move into and from the collection container; a drainage tube configured to urge a fluid from the catheter to the collection container; a gas suction line; and a removable adapter comprising a port configured to couple with the gas suction line and with the vent of the collection container, and wherein the gas suction line is configured to remove gas from the collection container through the removable adapter.

In some embodiments, the vent of the collection container is an outlet vent configured to passively expel displaced air. In some embodiments, the removable adapter comprises a gap through which the port passes so as to couple with the vent of the collection container. In some embodiments, the collection container comprises a lid, wherein the vent of the collection container is positioned on the lid, and wherein the adapter is configured to couple with the vent by a sliding motion parallel to the lid. In some embodiments, the collection container is configured to collect a fluid comprising urine. In some embodiments, the collection container comprises a groove, and wherein the removable adapter comprises a ridge to couple with the groove. In some embodiments, the port is further configured to automatically lock around the vent in response to the adapter being attached to the vent by a sliding motion. In some embodiments, the collection container comprises a lid, wherein the vent is positioned on the lid, and wherein the adapter is configured to attach with the vent by a sliding motion at least substantially perpendicular to the lid. In some embodiments, the port is configured to seal around the vent of the collection container. In some embodiments, the port is configured to rotate in a circular direction to seal around the vent. In some embodiments, the port of the adapter is configured to seal around the vent by at least one of a rotation into an open position; torsional rotation; a snap fit connection; or a living hinge.

In some embodiments, a system, comprises a fluid collection container comprising a vent; and an adapter comprising: a housing comprising an interior and at least one connecting structure provided with the interior to couple with the fluid collection container; and a port movable between a first position and a second position, wherein the port is configured to couple with the vent when the at least one connecting structure is engaged with the fluid collection container.

In some embodiments, the vent of the fluid collection container is an outlet vent configured to passively expel displaced gas. In some embodiments, the fluid collection container further comprises a lid, wherein the vent of the fluid collection container is positioned on the lid, and wherein the adapter is configured to couple with the vent when the connecting structure of the housing of the adapter is slid over at least a portion of the lid. In some embodiments, the fluid collection container is configured to collect a fluid comprising urine. In some embodiments, the fluid collection container comprises a lid, wherein the vent is positioned on the lid, and wherein the adapter is configured to attach with the vent by a sliding motion at least substantially perpendicular to the lid. In some embodiments, the port of the adapter is configured to seal around the vent of the fluid collection container. In some embodiments, the port of the adapter is configured to rotate in a vertical direction to seal around the vent of the fluid collection container. In some embodiments, the port of the adapter is configured to seal around the vent by at least one of a rotation into an open position; torsional rotation; a snap fit connection; or a living hinge. In some embodiments, the system further comprises a gas suction line connected to the adapter to remove gas from the fluid collection container when the port is in the second position. In some embodiments, the system further comprises a collection bag coupled to the vent of the fluid collection container, and wherein the gas suction line is configured to remove gas from the collection bag. In some embodiments, wherein the port of the adapter is further configured to lock around the vent in response to the port coupling with the vent.

DRAWINGS

A more particular description of the present disclosure will be rendered by reference to specific embodiments thereof that are illustrated in the appended drawings. It is appreciated that these drawings depict only typical embodiments of the invention and are therefore not to be considered limiting of its scope. Example embodiments of the invention will be described and explained with additional specificity and detail through the use of the accompanying drawings in which:

FIG. 1C illustrates a cross-sectional side view of a proximal pump of the fluid drainage system of FIG. 1A, in some embodiments.

DESCRIPTION

Figure 1A:
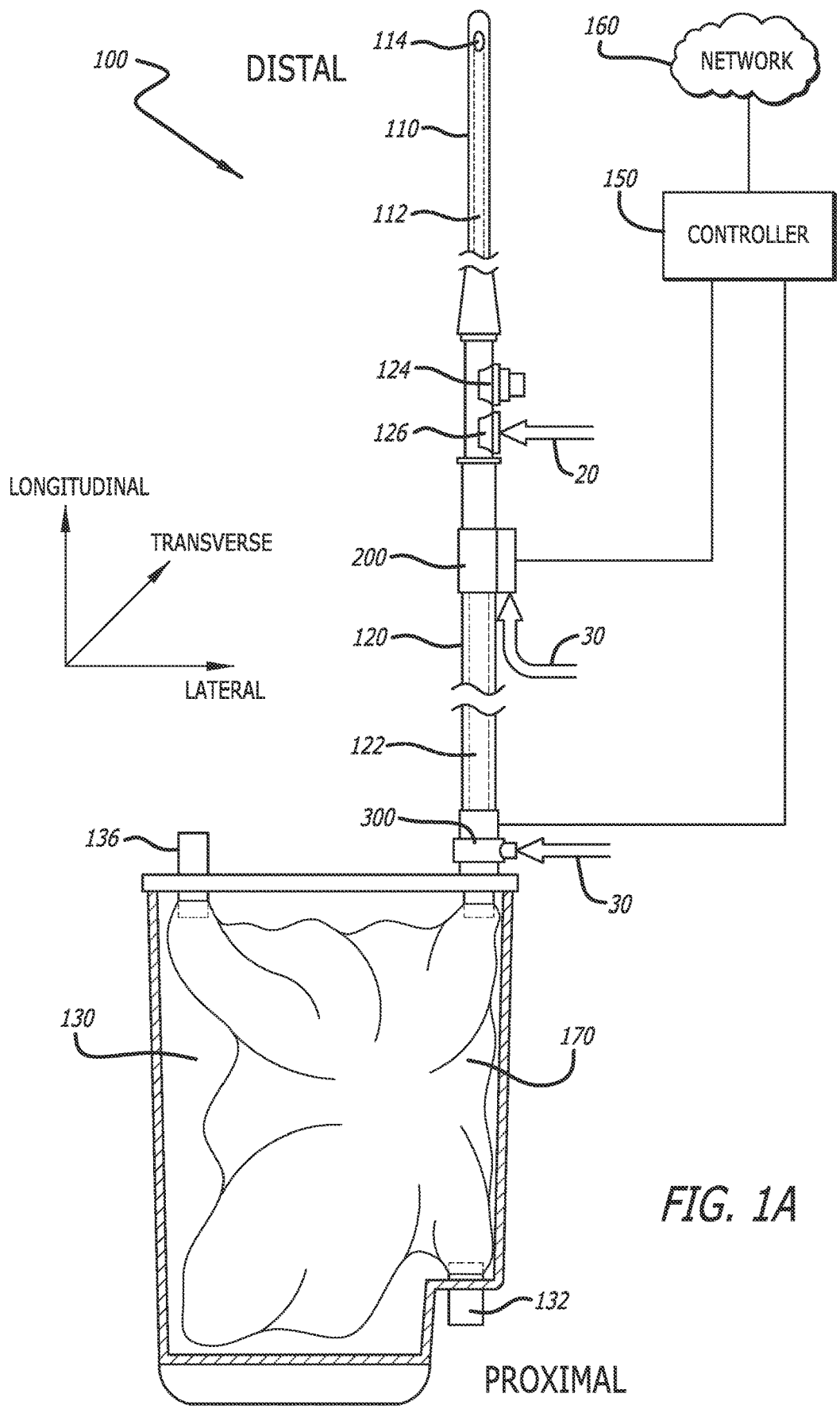
FIG. 1A illustrates an exemplary fluid drainage system including a distal pump and a proximal pump, in some embodiments.

Before some particular embodiments are disclosed in greater detail, it should be understood that the particular embodiments disclosed herein do not limit the scope of the concepts provided herein. It should also be understood that a particular embodiment disclosed herein can have features that can be readily separated from the particular embodiment and optionally combined with or substituted for features of any of a number of other embodiments disclosed herein.

Regarding terms used herein, it should also be understood the terms are for the purpose of describing some particular embodiments, and the terms do not limit the scope of the concepts provided herein. Ordinal numbers (e.g., first, second, third, etc.) are generally used to distinguish or identify different features or steps in a group of features or steps, and do not supply a serial or numerical limitation. For example, "first," "second," and "third" features or steps need not necessarily appear in that order, and the particular embodiments including such features or steps need not necessarily be limited to the three features or steps. Labels such as "left," "right," "top," "bottom," "front," "back," and the like are used for convenience and are not intended to imply, for example, any particular fixed location, orientation, or direction. Instead, such labels are used to reflect, for example, relative location, orientation, or directions. Singular forms of "a," "an," and "the" include plural references unless the context clearly dictates otherwise.

With respect to "proximal," a "proximal portion" or a "proximal end portion" of, for example, a catheter disclosed herein includes a portion of the catheter intended to be near a clinician when the catheter is used on a patient. Likewise, a "proximal length" of, for example, the catheter includes a length of the catheter intended to be near the clinician when the catheter is used on the patient. A "proximal end" of, for example, the catheter includes an end of the catheter intended to be near the clinician when the catheter is used on the patient. The proximal portion, the proximal end portion, or the proximal length of the catheter can include the proximal end of the catheter; however, the proximal portion, the proximal end portion, or the proximal length of the catheter need not include the proximal end of the catheter. That is, unless context suggests otherwise, the proximal portion, the proximal end portion, or the proximal length of the catheter is not a terminal portion or terminal length of the catheter.

With respect to "distal," a "distal portion" or a "distal end portion" of, for example, a catheter disclosed herein includes a portion of the catheter intended to be near or in a patient when the catheter is used on the patient. Likewise, a "distal length" of, for example, the catheter includes a length of the catheter intended to be near or in the patient when the catheter is used on the patient. A "distal end" of, for example, the catheter includes an end of the catheter intended to be near or in the patient when the catheter is used on the patient. The distal portion, the distal end portion, or the distal length of the catheter can include the distal end of the catheter; however, the distal portion, the distal end portion, or the distal length of the catheter need not include the distal end of the catheter. That is, unless context suggests otherwise, the distal portion, the distal end portion, or the distal length of the catheter is not a terminal portion or terminal length of the catheter.

In the following description, certain terminology is used to describe aspects of the invention. For example, in certain situations, the term "logic" is representative of hardware, firmware or software that is configured to perform one or more functions. As hardware, logic may include circuitry having data processing or storage functionality. Examples of such circuitry may include, but are not limited or restricted to a hardware processor (e.g., microprocessor with one or more processor cores, a digital signal processor, a programmable gate array, a microcontroller, an application specific integrated circuit "ASIC," etc.), a semiconductor memory, or combinatorial elements.

Alternatively, logic may be software, such as executable code in the form of an executable application, an Application Programming Interface (API), a subroutine, a function, a procedure, an applet, a servlet, a routine, source code, object code, a shared library/dynamic load library, or one or more instructions. The software may be stored in any type of a suitable non-transitory storage medium, or transitory storage medium (e.g., electrical, optical, acoustical or other form of propagated signals such as carrier waves, infrared signals, or digital signals). Examples of non-transitory storage medium may include, but are not limited or restricted to a programmable circuit; semiconductor memory; non-persistent storage such as volatile memory (e.g., any type of random access memory "RAM"); or persistent storage such as non-volatile memory (e.g., read-only memory "ROM," power-backed RAM, flash memory, phase-change memory, etc.), a solid-state drive, hard disk drive, an optical disc drive, or a portable memory device. As firmware, the executable code may be stored in persistent storage.

The term "computing device" should be construed as electronics with the data processing capability and/or a capability of connecting to any type of network, such as a public network (e.g., Internet), a private network (e.g., a wireless data telecommunication network, a local area network "LAN", etc.), or a combination of networks. Examples of a computing device may include, but are not limited or restricted to, the following: a server, an endpoint device (e.g., a laptop, a smartphone, a tablet, a "wearable" device such as a smart watch, augmented or virtual reality viewer, or the like, a desktop computer, a netbook, a medical device, or any general-purpose or special-purpose, user-controlled electronic device), a mainframe, internet server, a router; or the like.

A "message" generally refers to information transmitted in one or more electrical signals that collectively represent electrically stored data in a prescribed format. Each message may be in the form of one or more packets, frames, HTTP-based transmissions, or any other series of bits having the prescribed format.

The term "computerized" generally represents that any corresponding operations are conducted by hardware in combination with software and/or firmware.

As shown in FIG. 1A, and to assist in the description of embodiments described herein, a longitudinal axis extends substantially parallel to an axial length of a catheter/drainage tube. A lateral axis extends normal to the longitudinal axis, and a transverse axis extends normal to both the longitudinal and lateral axes. It is appreciated that the fluid drainage systems described herein may be configured in one of many different ways, analogous examples of which can be found in U.S. Provisional Pat. App. No. 63/065,914 titled "Assisted Fluid Drainage System," which is incorporated herein by reference in its entirety.

Unless defined otherwise, all technical and scientific terms used herein have the same meaning as commonly understood by those of ordinary skill in the art.

FIG. 1A illustrates an exemplary fluid drainage system including a distal pump and a proximal pump, in some embodiments. FIG. 1A shows an exemplary assisted fluid collection system ("system") 100, which generally includes a catheter 110, a drainage tube ("tube") 120, and a collection container ("container") 130 including a collection bag 170. Exemplary catheters 110 include indwelling catheters, Foley catheters, balloon catheters, peritoneal drainage catheters, external catheters or the like, and are configured to be inserted into an orifice within the body of a patient to drain a fluid therefrom. Exemplary body fluids can include urine, blood, interstitial fluid, peritoneal fluid, saliva, mucus, or the like. In an embodiment, the catheter 110 can be inserted through the urethra and into a bladder of a patient. The catheter 110 includes an eyelet 114 that provides fluid communication with a lumen of the catheter 110, and is configured to drain a fluid, e.g. urine.

The drainage tube 120 extends from a proximal end of the catheter 110 to a collection container 130. The drainage tube 120 defines a drainage lumen 122 that provides fluid communication between the catheter lumen 112 and the collection container 130.

The drainage tube 120 can be formed of rubber, plastic, polymer, silicone, or similar suitable material. The collection container 130 can include a rigid container, a flexible collection bag (e.g., with regard to the embodiment of FIG. 1A, a collection bag 170), or similar suitable container for receiving a fluid, e.g. urine, drained from the catheter 110. In an embodiment, the container 130 includes a drainage outlet 132 to allow the fluid to be emptied from the collection container 130 and/or collection bag 170. In an embodiment, a lid (e.g., a meter lid) of the container 130 includes an outlet vent 136 configured to allow air or similar gas to be released from the collection container 130. In an embodiment, the outlet vent 136 can include a filter, valve, or similar structure configured to allow gas to escape from the container but to prevent a liquid from passing through the outlet vent 136.

In an embodiment, the drainage tube 120 can include one or more vacuum pumps, such as a first, distal vacuum pump ("distal pump") 200 disposed in-line with the lumen of the drainage tube 120 proximate a distal end of the tube 120, and a second, proximal vacuum pump ("proximal pump") 300 disposed in-line with the lumen 122 of the drainage tube 120 proximate a proximal end of the tube 120. It will be appreciated that additional vacuum pumps disposed therebetween are also contemplated to fall within the scope of the present invention. In an embodiment, the one or more vacuum pumps, e.g. pumps 200, 300, can be identical. In an embodiment, the one or more vacuum pumps, e.g. pumps 200, 300, can differ in size, configuration, vacuum pump characteristics, flow resistance characteristics, combinations thereof, or the like.

The drainage tube 120 can further include a sample port 124 or an inlet air vent 126. The sample port 124 can include a cap, valve or similar structure configured to allow selective access to the drainage tube lumen 122 to sample a fluid disposed therein. The inlet vent 126 can include a cap, valve or similar structure configured to allow air or a gas to enter the drainage lumen 122 but to prevent air, gas, or fluid from escaping from the drainage lumen 122. In an embodiment, the sample port 124 and the inlet vent 126 can be separate structures. In an embodiment, the sample port 124 and the inlet vent 126 can be the same structure. In an embodiment, the drainage tube 120 can include one or more of the sample port 124 or inlet vents 126. As shown in FIG. 1A, the sample port 124 and the inlet vent 126 can be disposed proximate a distal end of the drainage tube 120 and can be disposed distally of the distal pump 200. However, it will be appreciated that one or more of the sample port(s) 124 or the inlet vent(s) 126 can be disposed at other positions along the length of the drainage tube, for example between the distal pump 200 and the proximal pump 300, or proximal of the proximal pump 300.

Figure 1B:
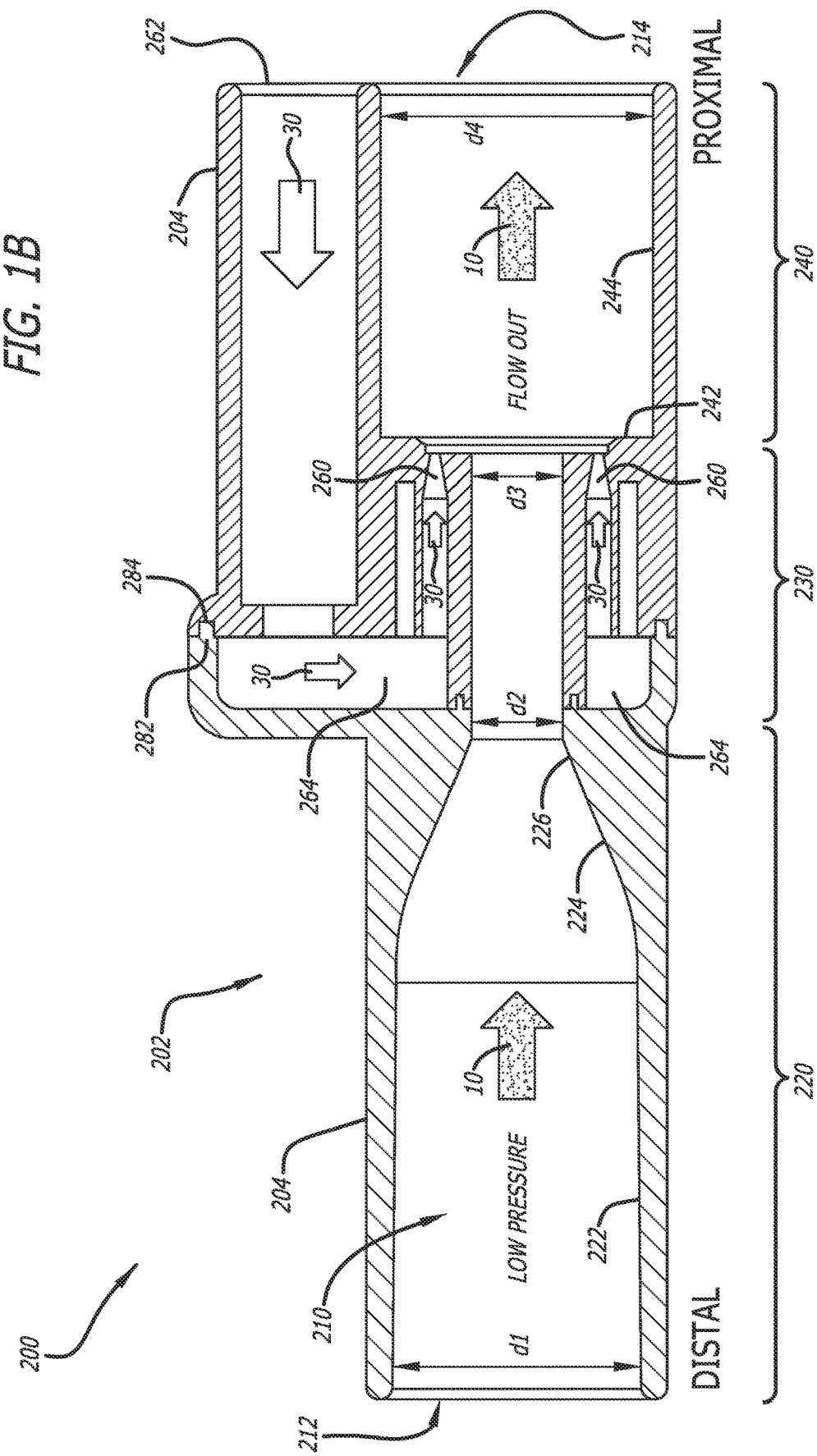
FIG. 1B illustrates a cross-sectional side view of a distal pump of the fluid drainage system of FIG. 1A, in some embodiments.

FIG. 1B illustrates a cross-sectional side view of a distal pump of the fluid drainage system of FIG. 1A, in some embodiments. FIG. 1B shows details of a first vacuum pump 200 disposed proximate a distal end of the drainage tube 120. The distal pump 200 can be an ejector pump that feeds a pressurized drive fluid 30 into a drainage lumen 210 to entrain a fluid, e.g. a drainage fluid 10, disposed within the drainage lumen 210. As used herein, the drainage fluid 10 can be a gas, liquid, or a mixed combination thereof, such as a vapor, or droplets of liquid mixed with gas. The distal pump 200 can include a housing 202 formed of a first housing piece 204 and a second housing piece 206. In an embodiment, the first housing piece 204 is disposed distally of the second housing piece 206. A distal surface of the first housing piece 204 can engage a proximal surface the second housing piece 206 to form the housing 202. The first housing piece 204 can be attached to the second housing piece 206 using adhesive, bonding, welding, or the like. Further, one of the first housing piece 204 or the second housing piece 206 can include a protrusion 282, configured to engage a recess 284 disposed on the opposing piece to align and secure the first housing piece 204 with the second housing piece 206. However, it will be appreciated that various numbers or configurations of protrusions 282 and recesses 284 are contemplated. Further, it will be appreciated that various attachment mechanisms including lugs, clips, snap-fit, interference fit, press fit engagements, or combinations thereof, are also contemplated to fall within the scope of the present invention. In an embodiment, the housing 202 can be formed as a single unitary piece by injection molding, 3D printing, or similar suitable means.

The distal vacuum pump 200 can include a drainage lumen 210 extending along a longitudinal axis from a drainage inlet 212 disposed at a distal end to a drainage outlet 214 disposed at a proximal end. The drainage lumen 210 can define a substantially circular cross-sectional shape. However, it will be appreciated that other cross-sectional shapes are also contemplated including square, triangular, hexagonal or any closed curve, regular or irregular polygonal shapes. In an embodiment, the cross-sectional shape can define a radially symmetrical shape.

In an embodiment, the inlet 212 can be releasably coupled with a distal portion of the drainage tube 120. In an embodiment, the inlet 212 can be integrally formed with a distal portion of the drainage tube 120. In an embodiment, the drainage outlet 214 can be releasably coupled with a proximal portion of the drainage tube 120. In an embodiment, the outlet 214 can be integrally formed with a distal portion of the drainage tube 120. As such, the drainage lumen 210 of the distal vacuum pump 200 can be disposed in-line a lumen 122 of the drainage tube 120.

The drainage lumen 210 of the distal vacuum pump 200 can include a converging section 220, a diffuser section 230, and a diverging section 240. The converging section 220 can extend from the drainage inlet 212 to a distal end of the diffuser section 230. The diffuser section 230 can extend from a proximal end of the converging section 220 to a distal end of the diverging section 240. The diverging section 240 can extend from a proximal end of the diffuser section 230 to a drainage outlet 214.

The drainage lumen 210 of the converging section 220 can define a first diameter (d1) proximate the drainage inlet 212 and a second diameter (d2), less than the first diameter (d1) proximate the diffuser section 230. In an embodiment, the drainage lumen 210 of the converging section 220 can define a continuous change in diameter between the first diameter (d1) and second diameter (d2), i.e. defining a continuous, tapered, cone shape.

In an embodiment, the drainage lumen 210 of the converging section 220 can define a discontinuous change in diameter between the first diameter (d1) and second diameter (d2). For example, as shown in FIG. 1B, the converging section 220 can include an accumulation portion 222 that defines a gradual reduction in diameter from the first diameter (d1), such that a wall of the accumulation portion 222 extends at a shallow angle of between 1° and 5°, relative to the longitudinal axis. However, greater or lesser angles are also contemplated. In an embodiment, a wall of the accumulation portion 222 can extend parallel to a longitudinal axis.

The distal vacuum pump 200 can further include a drive nozzle 260. In an embodiment, the drive nozzle 260 can define a ring-shaped cross-section extending annularly about the diffuser section 230, when viewed in cross-section to the longitudinal axis. In an embodiment, the drive nozzle 260 can include an array of nozzles arranged in a ring shape extending annularly about the diffuser section 230, when viewed in cross-section to the longitudinal axis.

The distal vacuum pump 200 can include a drive fluid inlet 262 that can provide a pressurized drive fluid 30 to a plenum 264. The plenum 264 can provide the pressurized drive fluid 30 to the drive nozzle 260. In an embodiment, the drive fluid 30 can include pressurized air, however, any suitable pressurized gas or liquid are also contemplated. In an embodiment, the drive fluid 30 can be provided by a separate line. In an embodiment, the drainage tube 120 can include a dual lumen, a first lumen can define the drainage lumen 122, a second lumen can provide a pressurized drive fluid 30 to one or more vacuum pumps, e.g. the distal pump 200 or proximal pump 300.

In an exemplary method of use, a drive fluid 30 is provided to the drive fluid inlet 262 and supplied through the plenum 264 to the drive nozzle 260. The drive nozzle 260 is designed to provide a drive jet into the divergent section 240 that entrains a drainage fluid 10, e.g. a gas, liquid, or mixed combination thereof, disposed within the drainage lumen 210. More specifically, the jet of drive fluid 30 is provided at a stepped portion 242 of the divergent section 240 that substantially aligns with a transition between the diffuser section 230 and the divergent section 240. The drive fluid 30 entrains a drainage fluid 10 disposed in the diffuser section 230 that creates a low pressure in the convergent section 220, which draws a drainage fluid 10 from the drainage inlet 212 proximally into the drainage lumen 210. Further, the drive jet 30 urges the drainage fluid 10 through the divergent section 240, through the drainage outlet 214 proximally into a proximal portion of the drainage tube 120.

Advantageously, the configuration of the drainage lumen 210 together with the drive jet 30 induces an amplifying effect, whereby a force of the pressurized drive fluid 30 is less than a suction force applied to the drainage fluid 10 at the drainage inlet 212. Advantageously, the distal vacuum pump 200 can draw either a columned drainage fluid 10 or a mixed drainage fluid 10 (e.g. liquid and gas mixture) from a distal portion of the drainage tube 120, disposed distally of the vacuum pump 200, through the drainage lumen 210, and urge the drainage fluid 10 proximally through the drainage tube 120.

FIG. 1C illustrates a cross-sectional side view of a proximal pump of the fluid drainage system of FIG. 1A, in some embodiments. FIG. 1C shows further details of the proximal vacuum pump 300. The proximal pump 300 can include a housing 302 formed of a first housing piece 304 and a second housing piece 306. In an embodiment, the first housing piece 304 is disposed distally of the second housing piece 306. A distal surface of the first housing piece 304 can engage a proximal surface the second housing piece 306 to form the housing 302.

The first housing piece 304 can be attached to the second housing piece 306 using adhesive, bonding, welding, or the like. Further, one of the first housing piece 304 or the second housing piece 306 can include a protrusion 382, configured to engage a recess 384 disposed on the opposing piece to align and secure the first housing piece 304 with the second housing piece 306. However, it will be appreciated that various numbers or configurations of protrusions 382 and recesses 384 are contemplated. Further, it will be appreciated that various attachment mechanisms including lugs, clips, snap-fit, interference fit, press fit engagements, or combinations thereof, are also contemplated to fall within the scope of the present invention. In an embodiment, the housing 302 can be formed as a single unitary piece by injection molding, 3D printing, or similar suitable means.

The proximal vacuum pump 300 can generally include a drainage lumen 310 extending along a longitudinal axis from a drainage inlet 312 disposed at a distal end to a drainage outlet 314 disposed at the proximal end. The drainage lumen 310 can define a substantially circular cross-sectional shape. However, it will be appreciated that other cross-sectional shapes are also contemplated including square, triangular, hexagonal or any closed curve, regular or irregular polygonal shapes. In an embodiment, the cross-sectional shape can define a radially symmetrical shape.

In an embodiment, the inlet 312 can be releasably coupled with a distal portion of the drainage tube 120. In an embodiment, the inlet 312 can be integrally formed with a distal portion of the drainage tube 120. In an embodiment, the outlet 314 can be releasably coupled with a proximal portion of the drainage tube 120. In an embodiment, the outlet 314 can be integrally formed with a distal portion of the drainage tube 120. As such, the drainage lumen 310 of the proximal vacuum pump 300 can be disposed in-line with a lumen 122 of the drainage tube 120.

The proximal vacuum pump 300 can include a converging section 320, a diffuser section 330, and a diverging section 340. The converging section 320 can extend from the drainage inlet 312 to a distal end of the diffuser section 330. The diffuser section 330 can extend from a proximal end of the converging section 320 to a distal end of the diverging section 340. The diverging section 340 can extend from a proximal end of the diffuser section 330 to a drainage outlet 314.

The drainage lumen 310 of the converging section 320 can define a first diameter (d1) proximate the drainage inlet 312 and a second diameter (d2), less than the first diameter (d1) proximate the diffuser section 330. In an embodiment, the drainage lumen 310 of the converging section 320 can define a continuous change in diameter between the first diameter (d1) and second diameter (d2) i.e. defining a continuous, tapered, cone shape.

In an embodiment, the drainage lumen 310 of the converging section 320 can define a discontinuous change in diameter between the first diameter (d1) and second diameter (d2). For example, as shown in FIG. 1C, the converging section 320 can include an accumulation portion 322 wherein a wall of the accumulation portion 322 extends substantially parallel to a longitudinal axis. In an embodiment, the accumulation portion 322 can define a gradual reduction in diameter from the first diameter (d1), such that a wall of the accumulation portion 322 extends at an angle of between 1° and 5°, relative to the longitudinal axis. However, greater or lesser angles are also contemplated.

The converging section 320 can also include a stepped portion 324 wherein an angle of the wall of the converging section 320 extends perpendicular relative to the longitudinal axis. The converging section 320 can also include an acceleration portion 326 that defines a greater reduction in diameter over a given longitudinal distance, than the accumulation portion 322, such that a wall of the acceleration portion 326 extends at an angle of between 10° and 40°, relative to the longitudinal axis. However, greater or lesser angles are also contemplated. It will be appreciated that embodiments of the converging section 320 can include various numbers, orders, and configurations of one of the accumulation portion 322, shoulder portion 324, or the acceleration portion 326.

In an embodiment, the drainage lumen 310 of the diffuser section 330 can define a substantially continuous diameter such that a diameter of the drainage lumen 310 at a distal end of the diffuser section 330, e.g. second diameter (d2) is substantially the same as a diameter of the drainage lumen 310 at a proximal end of the diffuser section 330, e.g. third diameter (d3). Worded differently, a wall of the drainage lumen 310 of the diffuser section 330 can extend substantially parallel to the longitudinal axis.

In an embodiment, the drainage lumen 310 of the diffuser section 330 can define a diverging diameter shape such that a diameter of the drainage lumen 310 at a distal end of the diffuser section 330, e.g. second diameter (d2) is less than a diameter of the drainage lumen 310 at a proximal end of the diffuser section 330, e.g. third diameter (d3). Worded differently, a wall of the drainage lumen 310 of the diffuser section 330 can extend at an angle relative to the longitudinal axis.

In an embodiment, the drainage lumen 310 of the diffuser section 330 can define a converging diameter shape such that a diameter of the drainage lumen 310 at a distal end of the diffuser section 330, e.g. second diameter (d2) is greater than a diameter of the drainage lumen 310 at a proximal end of the diffuser section 330, e.g. third diameter (d3). In an embodiment, the diffuser section 330 can define a continuous change in diameter between the second diameter (d2) and the third diameter (d3). In an embodiment, the diffuser section 330 can define a discontinuous change in diameter between the second diameter (d2) and the third diameter (d3).

The drainage lumen 310 of the diverging section 340 can define a diverging diameter shape diverging from the third diameter (d3) disposed proximate the distal end of the diverging section 340, to a fourth diameter (d4) disposed proximate the drainage outlet 314, the fourth diameter (d4) being greater than the third diameter (d3).

In an embodiment, the drainage lumen 310 of the diverging section 340 can define a continuous change in diameter between the third diameter (d3) and the fourth diameter (d4) e.g. to define an inverse tapering, cone shape relative to the direction of flow through the drainage lumen 310. In an embodiment, the drainage lumen 310 of the diverging section 340 can define a discontinuous change in diameter between the third diameter (d3) and the fourth diameter (d4). For example, the diverging section 340 can include a stepped expansion 342 in diameter of the drainage lumen 310 wherein a portion of the wall of the drainage lumen 310 extends perpendicular to the longitudinal axis. Further, the diverging section 340 can include an expansion portion 344 wherein a portion of the wall of the drainage lumen 310 can extend at an angle of between 1° and 5°, relative to the longitudinal axis. However, greater or lesser angles are also contemplated. In an embodiment, a wall of the expansion portion 344 can extend substantially parallel to a longitudinal axis.

It will be appreciated that embodiments of the diverging section 340 can include various numbers, orders, and configurations of stepped portions 342 or expansion portion 344. In an embodiment, one or more transition edges between the converging section 320, diffuser section 330, diverging section 340, or portions thereof, can include a chamfered edge.

The proximal vacuum pump 300 can further include a drive nozzle 360. In an embodiment, the drive nozzle 360 can define a ring shape extending annularly about the diffuser section 330, when viewed in cross-section to the longitudinal axis. In an embodiment, the drive nozzle 360 can include an array of nozzles arranged in a ring shape extending annularly about the diffuser section 330, when viewed in cross-section to the longitudinal axis.

The proximal vacuum pump 300 can include a drive fluid inlet 362 that can provide a pressurized drive fluid 30 to a plenum 364. The plenum 364 can provide the pressurized drive fluid 30 to the drive nozzle 360. In an embodiment, the drive fluid 30 can include pressurized air, however, any suitable pressurized gas or liquid are also contemplated.

In an embodiment, the distal pump 200 and the proximal pump 300 can be identical. In an embodiment, the distal pump 200 and the proximal pump 300 can be different, in either configuration and/or properties of the pump. For example, the pumps can differ in overall size, configuration of the drainage lumen profile, configuration of the drive nozzle/nozzle array, number of drive nozzles, drive fluid inlet resistance, combinations thereof, or the like.

In an embodiment, one of the distal or proximal pumps 200, 300, can be tuned differently from the other, such as providing a different vacuum force or providing greater or lesser volume movement, or the like. For example, a larger overall pump can provide a greater movement of volume of fluid. By contrast, an overall smaller pump, including identical proportions to the larger pump, can achieve a harder vacuum (lower absolute pressure). Further, individual pump characteristics can be further modified by modifying a volume or pressure of drive fluid 30 supplied thereto. As such each of the proximal pump 200 and the distal pump 300 can be tuned to provide specific pump characteristics for their respective location along the drainage tube 120.

In an exemplary method of use, a drive fluid 30 is provided to the drive fluid inlet 362 and supplied through the plenum 364 to the drive nozzle 360. The drive nozzle 360 provides a drive jet into the divergent section 340 that entrains a drainage fluid 10, e.g. a gas, liquid, or mixed combination thereof, disposed in the drainage lumen 310. More specifically, the jet of drive fluid 30 is provided at a stepped portion 342 of the divergent section 240 that substantially aligns with a transition between the diffuser section 330 and the divergent section 240. The drive fluid 30 entrains a drainage fluid 10 disposed in the diffuser section 330 that creates a low pressure in the convergent section 320, which draws a drainage fluid 10 from the drainage inlet 312, proximally through the drainage lumen 310. Further, the drive jet urges the drainage fluid 10 through the divergent section 340, proximally into a proximal portion of the drainage tube 120.

Among other things, the configuration of the drainage lumen 310 together with the drive jet 30 induces an amplifying effect, whereby a force of the pressurized drive fluid 30 is less than a suction force applied to the drainage fluid 10 at the drainage inlet 312. Advantageously, the proximal vacuum pump 300 can draw either a columned drainage fluid 10 or a mixed drainage fluid 10 (e.g. liquid and gas mixture) from a portion of the drainage tube 120, disposed distally of the proximal vacuum pump 300, through the drainage lumen 310, and urge the drainage fluid 10 proximally through the drainage tube 120 and into the collection container.

Among other things, the assisted fluid drainage system 100 including the ejector pumps 200, 300 can prevent the formation of dependent loops within the drainage lumen 122.

Among other things, the system 100 can operate under lower pressure conditions and does not require a valve to separate fluid communication between the catheter 110 and the drainage tube 120 during operation. The catheter 110, including columnized fluid disposed within the catheter lumen 112, can provide a greater flow resistance than a flow resistance of the inlet vent 126. As such the distal pump 200 creates a vacuum that entrains a fluid, which includes liquid disposed within the drainage lumen 122 and air from the inlet vent 126. The vacuum is not communicated through catheter 110 to the patient. Instead fluid from the catheter 110 can transfer (e.g. by gravity, diffusion, etc.) to the drainage lumen 122 before being entrained by the distal pump 200. Since the distal pump 200 operating at the lower pressure is unable to urge the fluid through the proximal portion of the drainage lumen 122, subsequent pumps disposed along the drainage lumen, e.g. proximal pump 300, can continue to urge the fluid through the drainage tube 120 to the collection container 130.

In an embodiment, the vacuum pumps 200, 300 can work in conjunction to urge a drainage fluid 10 through the drainage tube 120. The influence of a pump on a fluid within a pipe can be limited by a number of factors, e.g. fluid temperature, state, gas or fluid mix, incline, etc. As such the influence of a pump can be limited to a given longitudinal length. To overcome these limitations, a greater vacuum force can be applied by the pump to move a fluid from the catheter 110, through the drainage tube 120, and into the collection container 130. However, such a force can cause trauma to a patient, as such a catheter 110 must be disconnected from the drainage tube 120, e.g. by shutting a valve or the like, before the pump can clear the drainage line.

Embodiments disclosed herein teach one or more pumps 200, 300 disposed along the drainage tube 120. The pumps 200, 300 can operate at lower forces to allow the pumps to operate while the drainage tube 120 remains in fluid communication with the catheter 110. While the pumps 200, 300 operating at lower forces, have a shorter length of influence along the drainage lumen, the pumps 200, 300 can work in conjunction to influence the entire length of the drainage tube 120. As noted, high pump forces can have a detrimental effect on a patient should the catheter 110 remain in fluid communication with the drainage tube when a sufficient driver fluid force 30 is applied to a single pump to urge the drainage fluid 10 along an entire length of the drainage tube 120. As such, the catheter 110 must be fluidly disconnected, e.g. by shutting a valve, before such a pump can operate. By contrast, embodiments disclosed herein disclose two or more pumps operating at a lower driver fluid pressure 30 to urge a drainage fluid through a portion of the drainage lumen 122. An adjacent pump can then be configured to urge the drainage fluid 10 through an adjacent portion of drainage lumen 122.

Advantageously, embodiments described herein can operate to urge a drainage fluid 10 through the drainage lumen 122 while the catheter 110 remains in fluid communication with the drainage tube 120. This allows the pumps 200, 300 to operate continuously while the catheter 110 is in place, without requiring coordinated closing and opening of valves or starting/stopping a pumps. As such, the system 100 requires a simplified operation and manufacture, reducing associated costs.

As noted, a number of variables can affect the influence distance of a pump. In an embodiment, the pumps 200, 300 can be tuned such that adjacent influence distances (y) overlap under mixed drainage fluid conditions. If parameters of the drainage fluid change such that adjacent influence distances (y) do not overlap then drainage fluid 10 can potentially pool between pumps 200, 300. However, pooled fluid 10 provides a columnized fluid 10 that can cause the influence distance (y) to increase. As such the system 100 and pumps 200, 300 can be tuned to self-regulate.

In an embodiment, the one or more vacuum pumps 200, 300 can operate intermittently. In an embodiment, the system 100 can include a controller 150 configured to control operation of one or more vacuum pumps 200, 300. The controller include logic configured to operate one or more vacuum pumps 200, 300 continuously, intermittently, concurrently, sequentially, alternately, or combinations thereof. The controller 150 operate the pumps 200, 300 concurrently to move the drainage fluid 10 through the drainage tube 120. In an embodiment, the one or more pumps 200, 300 can be operated sequentially or alternately, to move a fluid 10 through the drainage tube 120 in a "wave-like" manner.

In an embodiment, the controller 150 can operate the pumps 200, 300 in response to a trigger. For example, the controller 150 can trigger operation of the one or more pumps 200, 300 in response to a given time interval elapsing, in response to an input such as the presence of liquid or an increase in fluid pressure within the drainage lumen, or combinations thereof. In an embodiment, the controller 150 can be communicatively coupled with a network 160, or similar external computing device such as an electronic health records system, intranet, mobile device, centralized or decentralized network or the like. This can allow a user to operate the controller 150 remotely, or receive information about the system 100.

Advantageously, the configuration of the pumps 200, 300 does not inhibit fluid flow through drainage tubes 120 even when the pumps are not operating. This allows the drainage system 100 to function as a gravity driven system when the pumps are not operating increasing power efficiency of the system 100. In an embodiment, atmospheric gas (air) 20 can be provided to the system 100 by way of the inlet vent 126. This atmospheric gas 20 can be mixed with the drainage fluid 10 and drawn through the drainage tube 120 into the container 130. The fluid 10 can then be collected in the container 130 and excess gas can be vented from the system 100 by way of outlet vent 136.

Figure 1D:
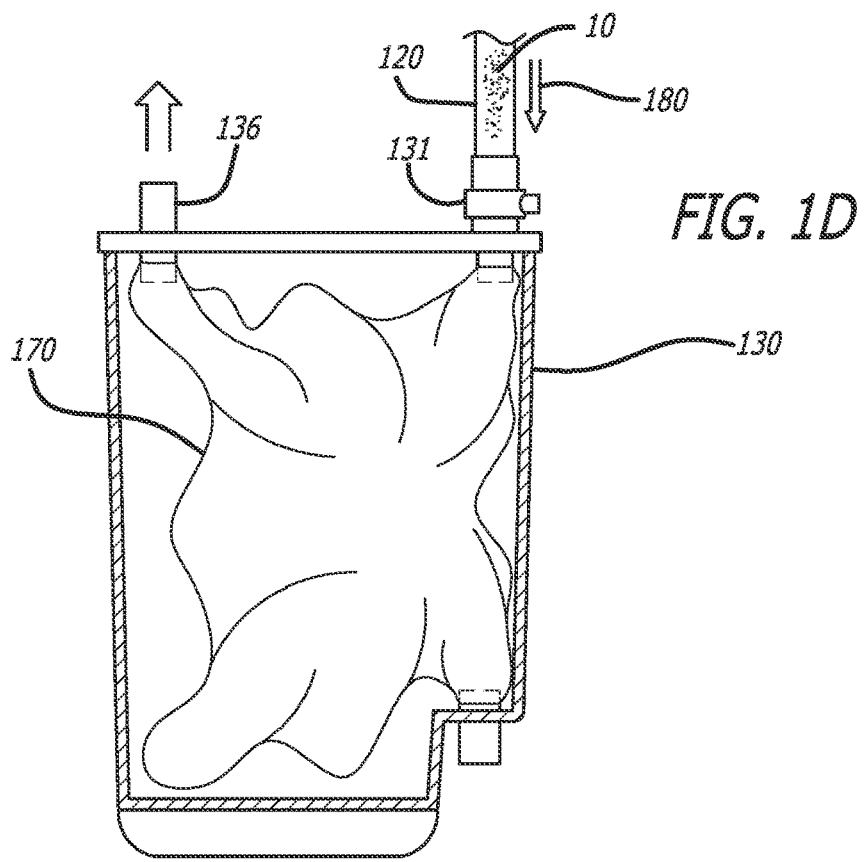
FIGS. 1D-1E illustrate inflation of a collection bag when a high flow-rate of air is utilized to transport fluid trapped within a drainage tube.
Figure 1E:
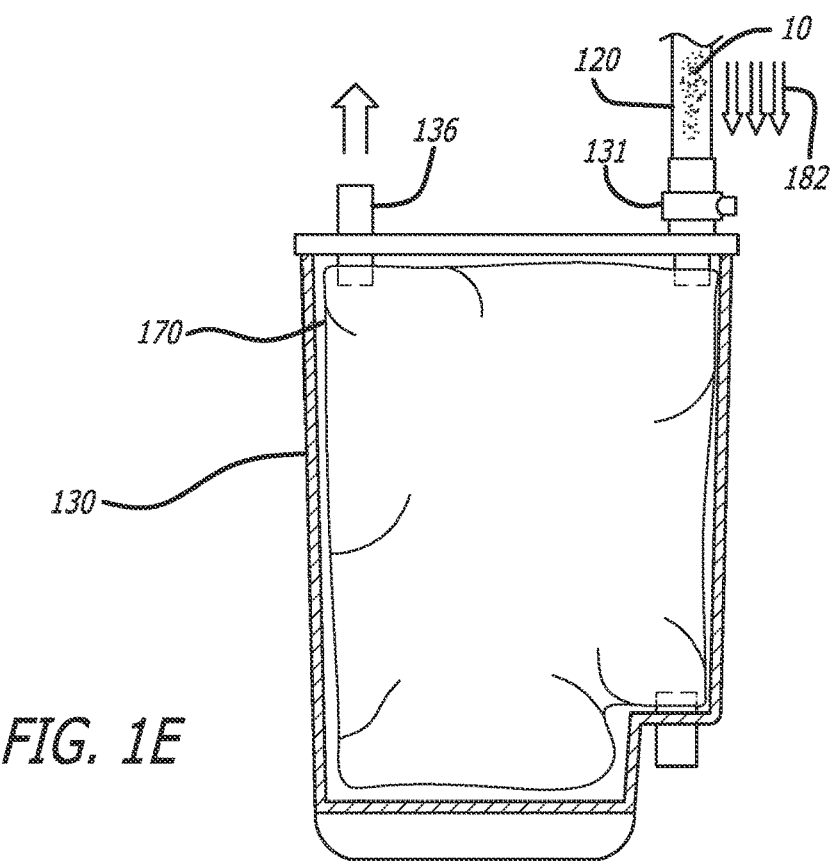

FIGS. 1D-1E illustrate inflation of a collection bag when a high flow-rate of air is utilized to transport fluid trapped within a drainage tube. In the embodiments of FIGS. 1D-1E, a collection container 130 includes a collection bag 170 for receiving a fluid (e.g., urine 10) which is drained from another source (e.g., with reference to FIG. 1A, the catheter 110) through the drainage tubing 120. The drainage tube 120 may be coupled to the container 130 at inlet port 131. During use, dependent loops of columnized urine may form within the drainage tubing 120 or residual urine may otherwise remain attached to an inner wall of the drainage tubing 120. To send this columnized fluid to the bag, an airflow 180 is provided (e.g., with reference to FIG. 1A, via inlet vent 126) for moving the urine 10 toward collection bag 170 as shown in FIG. 1D. In one embodiment, airflow 180 may be an air stream provided by an external source to the collection container 130 which moves the urine 10 column towards the collection bag 170.

In the example of FIG. 1D, the airflow 180 is provided at a relatively low rate compared to an increased rate as shown in FIG. 1E. The use of a low flow-rate of air to transport urine trapped in a dependent loop (e.g., as in FIG. 1D) may leave a relatively large amount of residual urine within the drainage tube 120 that cannot be cleared, compared to the use of the higher airflow 182 as shown in FIG. 1E. However, as shown in FIG. 1E, the increased airflow 182 may cause a corresponding inflation of the collection bag 170. While the examples of FIGS. 1D-1E include an outlet vent 136, the outlet vent 136 is configured to vent gas (e.g., air from the airflows 180, 182) passively and does not operate at a high enough flow-rate to keep the inflated collection bag 170 from inflating due to the increased airflow 182, as in FIG. 1E. Excessive inflation may cause inflated collection bag 170 to rupture, potentially contaminating collection container 130.

Figure 2A:
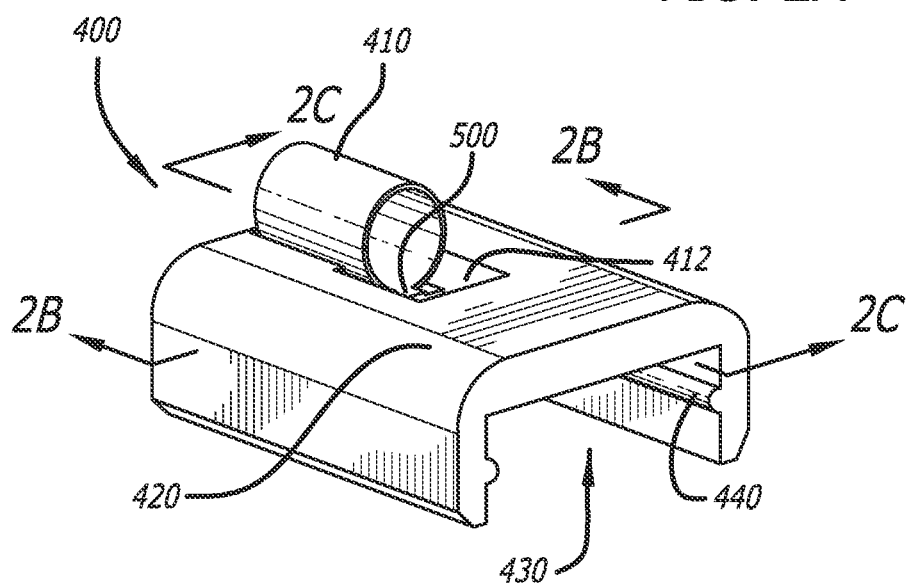
FIG. 2A shows a vent adapter for coupling with a suctioning airline and the fluid drainage system of FIG. 1A, in some embodiments.

FIG. 2A shows a vent adapter for coupling with a suctioning airline and the fluid drainage system of FIG. 1A, in some embodiments. In use, an adapter 400 may be coupled with a collection container (e.g., with reference to FIG. 1A, the collection container 130 coupled to the drainage tube 120). Furthermore, the adapter 400 may be coupled with a suctioning airline (as seen in FIG. 3B). When a high rate of air flow is used to transport columnized urine from the drainage tube 120 to the collection bag 170 within the collection container 130, a suctioning force removes air within the collection bag 170, reducing the risk of inflation thereof.

In the embodiment of FIG. 2A, the adapter 400 includes a port 410 configured to couple with a suctioning airline and is positioned in a cavity 412 of the adapter 400. The port 410 may be a hollow structure, e.g., a cylindrical structure, that acts as a lumen to allow fluid, e.g., air, to pass therethrough. The port 410 includes a distal end and a proximal end, where the distal end is configured to create a fluid seal with the housing 420 around the aperture 414, which in turn creates a fluid seal between the port 410 and a top surface 502 of the container 130 (see FIGS. 3A-4), as discussed below. In some embodiments disclosed herein, a living hinge 500 may couple the port 410 to a housing 420 of the adapter enabling rotation between a first and second position. In some embodiments as shown in FIGS. 2C-2D, the port 410 may be maintained in the upright position (e.g., as shown in FIG. 2D) in one of several methods. One such method includes the port 410 coupling to the housing 420 via a snap fitting where an exterior ridge 411 of the port 410 couples with a lip 415 of the housing 420. Thus, in such an example, the port 410 is moved from a first position (FIG. 2C) to a second position (FIG. 2D) such that force applied to the port 410 enables the coupling and decoupling of the portion 410 to the housing 420.

The adapter 400 further includes the housing 420, an interior cavity 430 (having an upper surface 416) and an interior ridge 440. The port 410 may rotate between a first position (e.g., in a flat position at least substantially aligned with the cavity 412 and a surface of the housing 420) and a second position (e.g., a raised position which is at least substantially perpendicular to the cavity 412 and/or a surface of the housing 420; however, the raised position need not be perpendicular to the cavity 412 and/or a surface of housing 420). In some embodiments, the port 410 is configured to rotate between the first position and the second position. In other embodiments, the port 410 is configured to only rotate to the second position from the first position, at which point the port 410 may be fixed. In some embodiments, the port 410 may be configured to accommodate multiple suctioning air lines at once.

In some embodiments, when in the second position (as seen in FIG. 2D), the port 410 may be configured for fluid communication with collection bag 170 disposed with the container 130, via outlet vent 136 of the container 130. For example, the port 410 may move from the first position to the second position and form a fluid seal with outlet vent 136 such that gas from the collection bag 170 may be expelled through outlet vent 136 into port 410, and into a suctioning airline coupled with port 410 (as seen in FIG. 3B). The port 410 may lock after reaching the second position, such as to prevent further rotation, e.g., rotate back into the first position. In some embodiments, the fluid seal may be formed by a vertical force against the outlet vent 136 created by port 410 rotating into the second position. In other embodiments the fluid seal may be formed by torsional rotation, a snap fit connection, or a living hinge mechanism.

To allow gas to pass from the outlet vent 136 of the container 130 into the port 410 of the adapter 400, the housing 420 may include an aperture 414 that aligns with an opening of the port 410 and the outlet vent 136 of the container 130. In some embodiments, when the port 410 is rotated, the port 410 will make contact with a predetermined portion of the cavity 412 having one or more gaps, vents, apertures, or openings through which gas can pass. For example, an aperture 414 may be provided in the cavity 412 which allows the port 410 to, when rotated, at least partially pass through the cavity 412 to the interior cavity 430. In one embodiment, when the port 410 is rotated into the second position, at least a portion of the port 410 may extend into the interior cavity 430 of the housing 420 so that a fluid seal is created between the adapter 400 and the container 130 that surrounds the outlet vent 136.

In one embodiment, when the port 410 is rotated into the aperture 414, the port 410 will rotate through the cavity 412 and physically contacts the container 130 to form a fluid seal over the outlet vent 136 so that a suctioning airline attached to port 410 may remove gas from outlet vent 136. In one embodiment, the housing 420 may be at least substantially gas permeable to allow gas to pass from the outlet vent 136 to the port 410.

In one embodiment, the port 410 may have a cylindrical shape. In some embodiments, the aperture 414 may be shaped and have dimensions at least substantially similarly to the port 410 (e.g., the port 410 may be cylindrical and the aperture 414 may be circular). In some embodiments, the port 410 may comprise a tube. The port 410 may have a length which is less than that of the cavity 412, so that in the first position, the port 410 will rest in the cavity 412. The port 410 may have a length which is greater than a depth of the cavity 412, so that when the port 410 is rotated into the second position, a first portion of the port will protrude above the upper surface of the housing 420, a second portion of the port will be within the aperture 414, and a third portion of the port will be below the housing 420. In some embodiments, the port 410 may be positioned in cavity 412 in the first position so that a first portion of the port 410 is above the aperture 414, such that as the port 410 rotates, the first portion and a first end of the port 410 enters into the aperture 414 while a second portion and a second end of port 410 rotates above aperture 414. In one embodiment, when the port 410 has finished rotating, the first portion and the first end of port 410 will be below the aperture 414 while the second portion and the second end will be above the aperture 414.

The first position may correspond to a storage position. The second position may correspond to a readied position, an open position, or a rotated position. For example, when the adapter 400 is stored in a packaging, the port 410 may be in the first position, and after removal from the packaging, a user may move port 410 from the storage position to the readied positioning. In some embodiments, the user may remove the adapter 400 from the packaging, slide adapter 400 onto the container 130, and move the port 410 from the storage position to the readied position.

In some embodiments, the port 410 may be configured for manual rotation by a user, e.g., after the collection container 130 and the adapter 400 are coupled. Among other things, a user may precisely control how the port 410 is readied for use. For example, a user may wish to leave the port 410 in a storage position while the adapter 400 is attached to the collection container 130 for transportation. In one embodiment, a user may slide the adapter 400 onto container 130 with port 410 in the storage position, and rotate port 410 into the readied position after adapter 400 has been slid onto container 130.

In some embodiments, the port 410 may be configured to automatically rotate from the storage position to the readied position, without user input. Configurations in which the port 410 rotates without requiring user input may enable the port 410 to be placed in a readied position while minimizing user error. In some embodiments, the adapter 400, the port 410 and/or the cavity 412 may include an axle, shaft, rod, living hinge, or other rotational mechanism enabling the port 410 to rotate. In some embodiments, the adapter 400 may couple with container 130 by sliding horizontally onto a lid of container 130 or collection bag 170. In other embodiments the adapter 400 may couple with container 130 by sliding vertically onto a lid of container 130 or collection bag 170.

In some embodiments, the cavity 412 may comprise a cradle, recess, nook or other structure to retain the port 410. The cavity 412 may include features to secure, retain, or hold the port 410. Furthermore, the adapter 400 and/or the cavity 412 may include features to prevent the port 410 from rotating. For example, the cavity 412 may include a restraint that prevents the port 410 from rotating until the adapter 400 begins coupling with collection container 130. In another embodiment, the cavity 412 may include a restraint that prevents the port 410 from rotating until the adapter 400 has coupled with collection container 130. In other embodiments, the cavity 412 may be free of features to prevent the port 410 from rotating.

In the embodiment of FIG. 2A, an interior cavity 430 of the adapter 400 includes a rounded ridge 440. The ridge 440 may be used to couple with a container 130, e.g. by sliding the ridge 440 onto an appropriate surface of the container 130. Ridge 440 may be configured to grip onto the surface of the container 130 so that adapter 400 is securely coupled to the container 130 and does not move or detach. Among other things, the secure coupling of adapter 400 to container 130 enables a seal between port 410 and outlet vent 136 to be preserved.

Figure 2B:
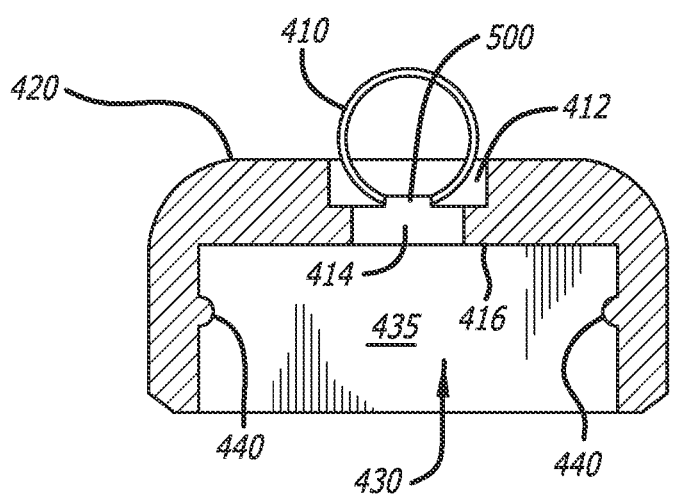
FIG. 2B shows a front view of the vent adapter of FIG. 2A, in some embodiments.
Figure 2C:
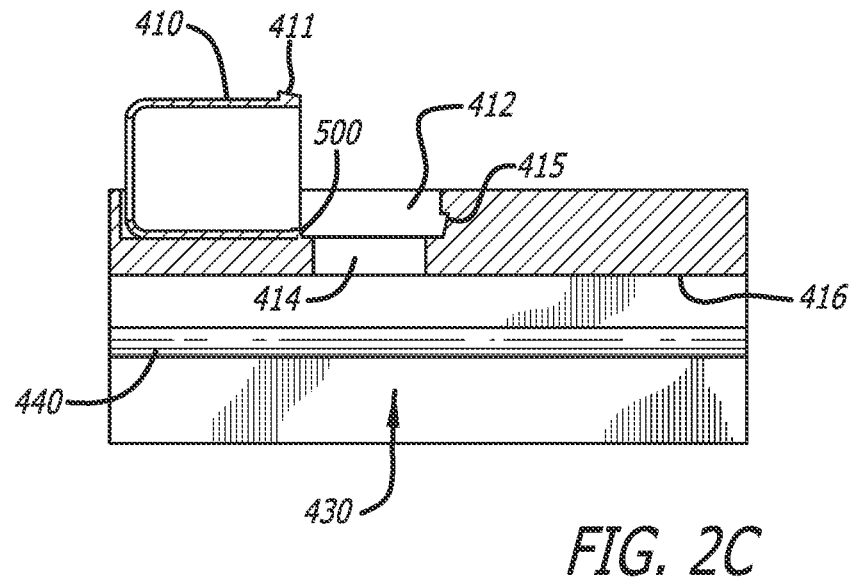
FIG. 2C shows a side view of the vent adapter of FIG. 2A, in some embodiments.
Figure 2D:
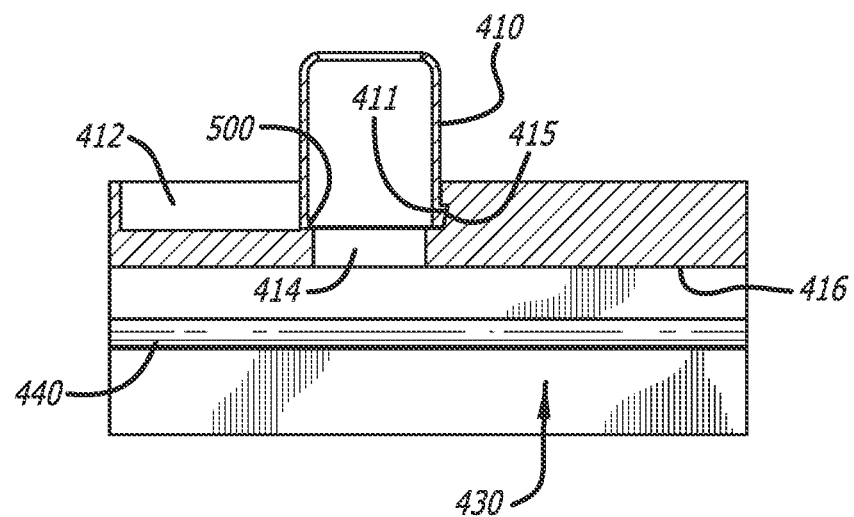
FIG. 2D shows a side view of the vent adapter of FIG. 2A, in some embodiments.

FIG. 2B shows a front view of the vent adapter of FIG. 2A, in some embodiments. The adapter 400 includes the port 410 positioned in cavity 412. In the embodiment of FIG. 2B, the port 410 is in a first flat position prior to rotation. The port 410 may be secured from moving laterally by its position in cavity 412. Furthermore, in the embodiment of FIG. 2B, the port 410 has a form factor which minimizes the height of the adapter 400 while the port 410 is in the first position. Among other things, the side profile of the adapter 400 may be flattened, and the form factor of adapter 400 at least partially preserved, compared to when port 410 is placed in the second position (e.g., a raised position).

In some embodiments, at least a portion of the port 410 may be sunken into the cavity 412 while port 410 is in the first position. The port 410 may have an angle in the first position which, among other things, facilitates storage and transportation of the adapter 400. For example, the port 410 may be flat, or it may be angled with an angle of, for example, 15°, 30°, 45°, 60°, etc. In some embodiments, the port 410 may be angled in the first position such that the distance needed for the port 410 to move into the second position is minimized. Among other things, the angle of the port 410 in the first position may enable the adapter 400 to be slid onto container 130. For example, in one embodiment, the port 410 is kept in the first position while adapter 400 is slid over container 130. In some embodiments, the adapter housing 420 may have a closed end 435 as shown in FIG. 2B.

FIG. 2C shows a side view of the vent adapter of FIG. 2A, in some embodiments. In one embodiment, the vent adapter 400 includes the port 410, which has been rotated to pass through adapter 400 into a readied position. When the port 410 is rotated into a readied position such as in FIG. 2C, the port 410 is configured to apply a vertical force against a surface below the port 410 (e.g., with reference to FIG. 1A, outlet vent 136). After the port 410 is rotated into the readied position, the port 410 will seal around the outlet vent 136 of a container 130. It may be appreciated that the port 410 may seal against surfaces such as the outlet vent 136 in other ways, including torsional rotation, a snap fit connection, or a living hinge. In some embodiments, the port 410 is integrated into the adapter 400. In other embodiments, port 410 couples with adapter 400 separately (e.g., after the adapter 400 is coupled to the container 130).

FIG. 2D shows a side view of a vent adapter, in some embodiments. The port 410 is in the second position (e.g., readied position) and extends through the aperture 414 in the cavity 412. In some embodiments, the port 410 may extend through the aperture 414 to form a sealed coupling with a container and vent gases therefrom (e.g., with reference to FIG. 1A, container 130). The aperture 414 may help hold the port 410 in place to enforce a seal formed by the port 410. In some embodiments, the port 410 may rotate in an opposite direction to the direction used to rotate into the second position, and thereby return to the first position such as in FIG. 2C.

Figure 3A:
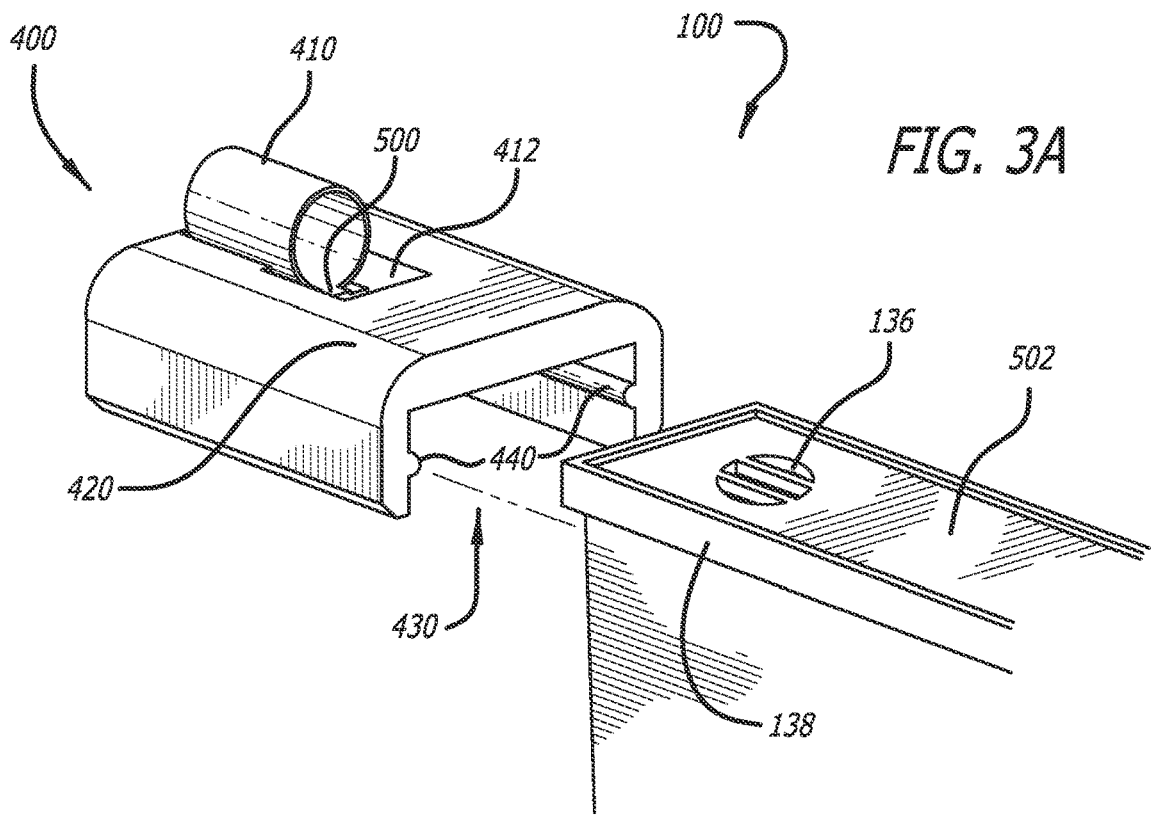
FIGS. 3A-3B illustrate the coupling of the vent adapter of FIG. 2A with the fluid collection system of FIG. 1A, in accordance with some embodiments.
Figure 3B:
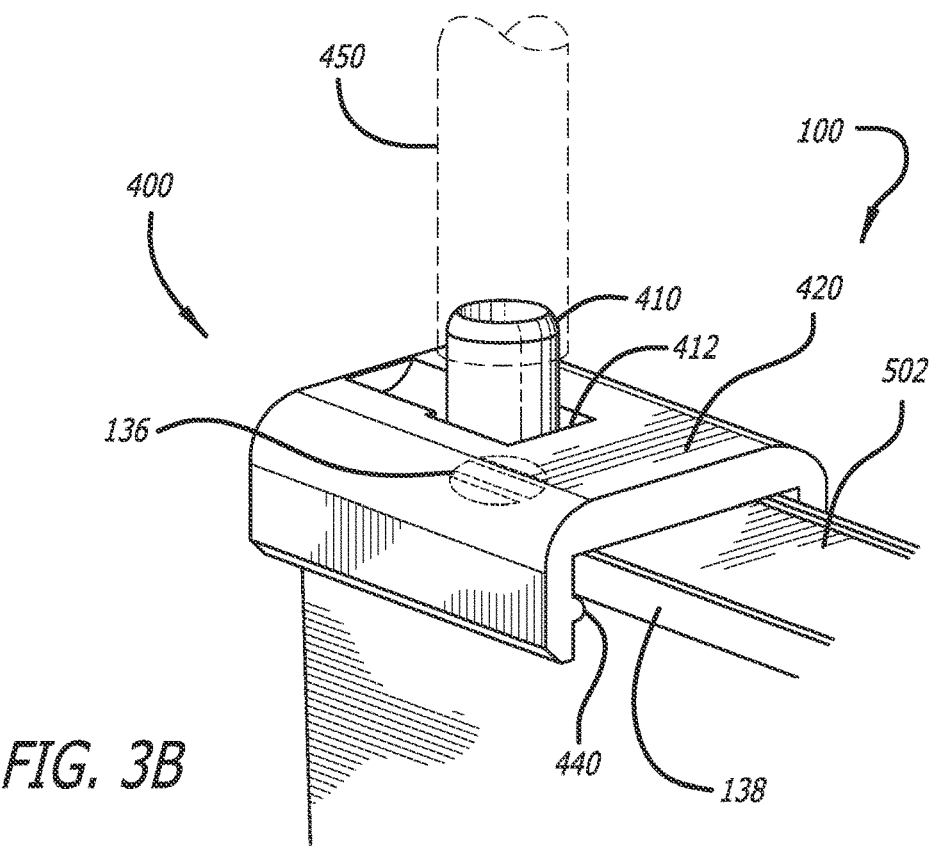

FIGS. 3A-3B illustrate the coupling of the vent adapter of FIG. 2A with the fluid collection system of FIG. 1A, in accordance with some embodiments. The fluid collection system 100 includes a container 130 and adapter 400. The container 130 includes an outlet vent 136 and rim 138. The adapter 400 includes a port 410, a cavity 412, an aperture 414 in the cavity 412, a housing 420, an interior cavity 430 and a ridge 440. In use, the ridge 440 of adapter 400 may be slid onto the rim 138 of the container 130 so that the adapter 400 and the container 130 are removably coupled. Before, during or after the adapter 400 and container 130 are coupled, the port 410 may be rotated from a horizontal position flush with the cavity 412 to a vertical position so as to seal with the outlet vent 136 once the adapter 400 and container 130 are coupled. The proximal end of the port 410 may form a fluid seal with the suctioning airline 450 (e.g., provided by a separate air suction system) to provide a suction force to remove gas (e.g., air) within the container 130. In some embodiments, the container 130 may include a container 130 and collection bag 170 (e.g., with reference to FIGS. 1A-1E). For example, with reference to FIG. 1E, gas may be removed from an inflated collection bag 170 (not shown), where the bag 170 has been inflated by an increased airflow to remove fluid from a drainage tube 120.

After use, the adapter 400 may be removed and disposed of by a user, or left coupled with the container 130 for further use. As shown by the embodiment of FIG. 3A, the removable adapter 400 and container 130 may be separate before being coupled. For example, the removable adapter 400 and container 130 may be each stored in separate packaging, for use by a user.

As described elsewhere, gas may enter a drainage tubing 120. For example, with reference to FIG. 2, the drive fluid 30 may include pressurized air for entraining the drainage fluid 10. The drainage fluid 10 may also include at least a combination of gas and liquid, or gas by itself. Furthermore, gas may be provided from an external source (e.g., via inlet vent 126). The container 130 includes an outlet vent 136 configured to allow air or similar gas to be released from the container 130. The movement of gas (e.g., an air stream) allows for the movement of fluid (e.g., columnized urine) from the drainage tube 120, to the container 130 thereby, among other things, allowing for increased accuracy of measurements. The gas may then be removed from the container 130 by suction via adapter 400.

In some embodiments, the outlet vent 136 may allow gas to be vented passively. In further embodiments outlet may be configured to receive an adapter to allow gas to be suctioned out from the collection container at a faster rate than the passive release of gas. For example, in embodiments where the outlet vent 136 includes a filter, valve or similar structure to allow gas to escape from the container, the filter, valve or similar structure may be configured to receive the adapter.

In the embodiment of FIG. 3A, the container 130 includes a rim 138. The rim 138 provides a surface for coupling with the adapter 400 (e.g., via ridge 440). For example, in an embodiment as in FIG. 3A, the rim 138 may be configured to receive the adapter 400 when the ridge 440 of adapter 400 is slid onto the rim 138 of container 130. It will be appreciated that various configurations to couple container 130 with adapter 400 are contemplated, such as clips, snap-fit, interference fit, press fit engagements, or combinations thereof. In one embodiment, the ridge 440 will grasp rim 138 when adapter 400 is coupled to container 130.

The rim 138 provides a structure for coupling container 130 with the adapter 400. Among other things, rim 138 provides an available location for a user to attach the adapter 400 to container 130. Attaching adapter 400 to a surface of container 130 by the rim 138 may minimize the use of moving mechanical parts. As described further below, the use of rim 138 may also enable more precise positioning of the port 410 over the outlet vent 136.

It will be appreciated that the housing 420 and the ridge 440 may be configured to assist a user in positioning the port 410 over outlet vent 136. For example, the housing 420 and ridge 440 may each have a length which is less than a length of the rim 138. In some embodiments, wherein the housing 420 and/or ridge 440 are shorter than rim 138, in operation a user slides the ridge 440 onto rim 138 to couple the adapter 400 with the container 130, until the ridge 440 is completely attached to rim 138 (e.g., until ridge 440 can no longer slide), causing the port 410 to align and seal with outlet vent 136. The port 410 may thereby be automatically aligned with the outlet vent 136 as a consequence of sliding the adapter 400 and container 130 to couple with one another. Among other things, a user may couple the adapter 400 and container 130 by moving adapter 400 in a single direction (e.g., to slide adapter 400 onto container 130), and is enabled to align the port 410 with outlet vent 136 with minimal error.

FIG. 3B illustrates a coupling of the fluid collection system of FIG. 1A with the vent adapter of FIG. 2A, in accordance with some embodiments. A suctioning airline 450 is coupled to port 410. The housing 420 is positioned on top of the container 130. The port 410 has rotated through the aperture 414 to align with the outlet vent 136 of the container 130, located beneath the housing 420, and has formed a seal by physically contacting container 130. The outlet vent 136 may be connected to a collection bag 170 (not shown) in the container 130, for venting excess gas (e.g., air) from the collection bag 170 using a suctioning force provided by suctioning airline 450. For example, suctioning airline 450 may apply a suction force to draw gas out of a collection bag 170 of the container 130, and the gas will pass through outlet vent 136 and port 410 to the suctioning airline 450. In some embodiments, where a high air flow is used to move urine from a drainage line 120 to a collection bag 170, the air can be removed from the collection bag 170 to reduce inflation. Port 410 may be connected a suctioning airline line 450 so that, when the port 410 is aligned with outlet vent 136, gas is suctioned from the collection bag 170.

In some embodiments, the port 410 is configured to lock in place when rotated inside aperture 414. For example, the adapter 400 may include a locking mechanism which activates after port 410 is rotated into the second readied position, which prevents port 410 from rotating freely thereafter. A seal created by the port 410 will thereafter be maintained by the locked port 410. In some embodiments, the locking mechanism may be manually activated or deactivated by a user. In one embodiment, the port 410 will lock around the outlet vent 136 as port 410 is rotated (e.g., via a locking rotation) and the adapter 400 is slid over a lid of the container 130.

In one embodiment, the user may further remove the adapter 400 by sliding the attachment in an opposite direction to that which was used to initially couple the adapter 400 and the container 130 (e.g., by sliding ridge 440 off of the rim 138). Among other things, an adapter 400 may therefore be coupled to the container 130 by moving the adapter 400 in a single, linear motion in a first direction; and the adapter 400 may be removed from container 130 by a single, linear motion in an opposite second direction.

In some embodiments, the ridge 440 may have a length which is less than a length of the housing 420. When ridge 440 is slid over the rim 138, at least a portion of the housing 420 may extend beyond rim 138 and the container 130. For example, as illustrated in FIG. 3B, at least a portion of the housing 420 extends beyond rim 138. Among other things, a user may hold the portion to slide the adapter 400 onto the container 130, and to remove adapter 400 from container 130. In some embodiments, ridge 440 is configured so that adapter 400 is securely coupled to container 130 such that a user may hold the adapter 400 to move container 130.

Figure 4:
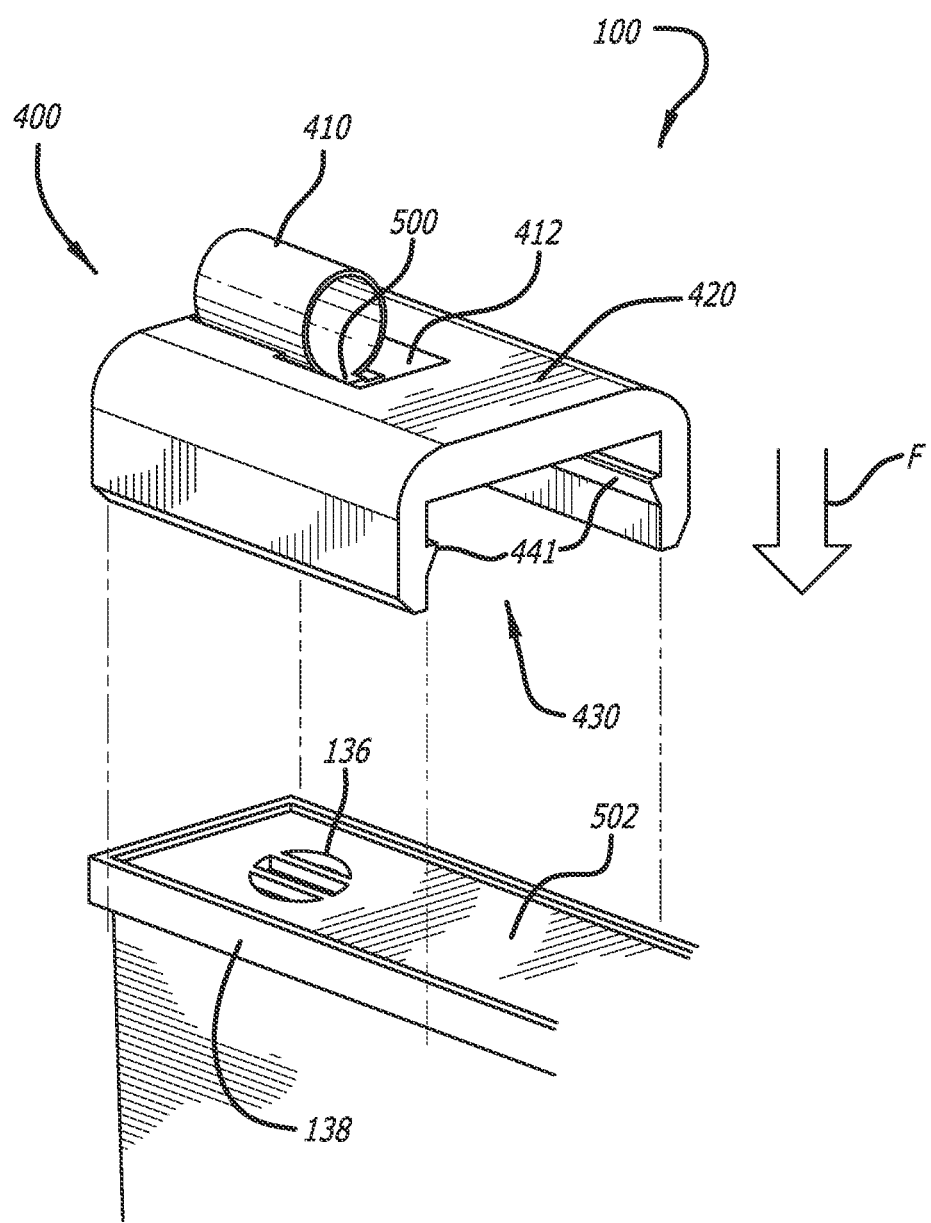
FIG. 4 illustrates a second embodiment of a vent adapter configured to couple with a collection container, in some embodiments.

FIG. 4 illustrate a second embodiment of a vent adapter configured to couple with a collection container, in some embodiments. In the embodiment of FIG. 4, the housing 420 of adapter 400 is configured for a snap fit with collection container 130. The housing 420 may be placed on the container 130, and pre-designated portions of housing 420 may snap onto edges of the collection container 130 facilitated by a tapered ridge 441. For example, the ridge 441 may have a tapered underside that facilitates coupling of the adapter 400 with the container 130 such that the rim 138 of the container 130 slides along the tapered underside. Further, the ridge 441 may have a flat (e.g., non-tapered) upper surface, which prevents the adapter 400 from easily uncoupling from the container 130.

In some embodiments, a user may align the port 410 with the outlet vent 136 when snapping the housing 420 onto container 130. Furthermore, in some embodiments, the housing 420 may be configured to assist a user in placing housing 420 so that the port 410 is aligned with the outlet vent 136. For example, the housing 420 and a lid of container 130 may have predetermined lengths such that when an end of housing 420 is aligned and placed on an edge of the lid of container 130, the port 410 will automatically be aligned with outlet vent 136.

In the embodiment of FIG. 4, the port 410 is in a first storage position in the cavity 412 of the housing 420. In the first storage position a length of the port 410 may rest horizontally on and be at least substantially flush with the surface of the cavity 412. After the housing 420 is placed and snapped onto the container 130, the port 410 may be rotated into a second position where the port 410 is at least substantially vertical relative to the cavity 412. A vertical force created by rotating the port 410 into the second position causes the port 410 to seal against outlet vent 136. In some embodiments, the rotation of port 410 further will cause port 410 to lock, so that after housing 420 is snapped onto the container 130, the port 410 will not rotate or lose the seal.

Figure 5A:
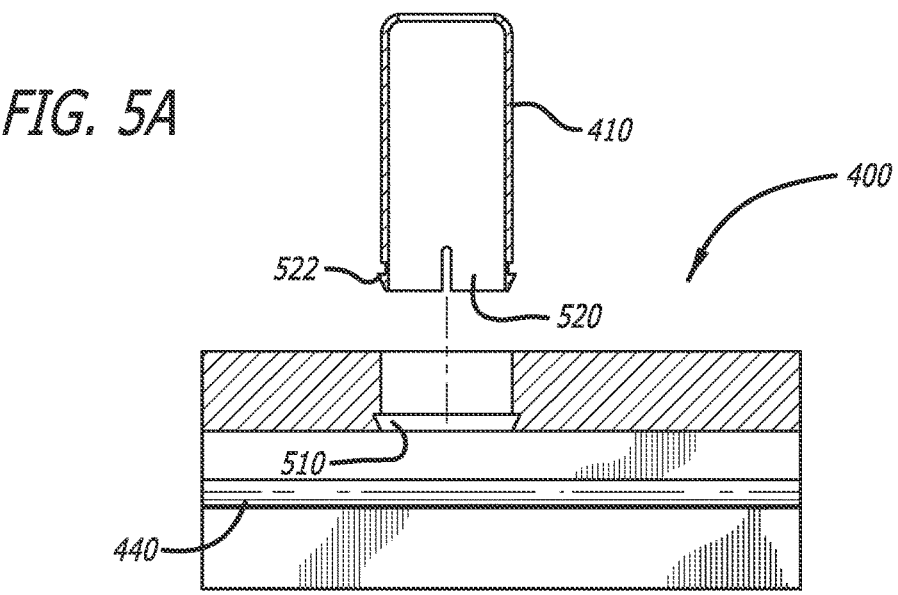
FIGS. 5A-5C illustrate cross-sections of alternative embodiments of vent adapters configured to couple with a collection container, according to some embodiments.
Figure 5B:
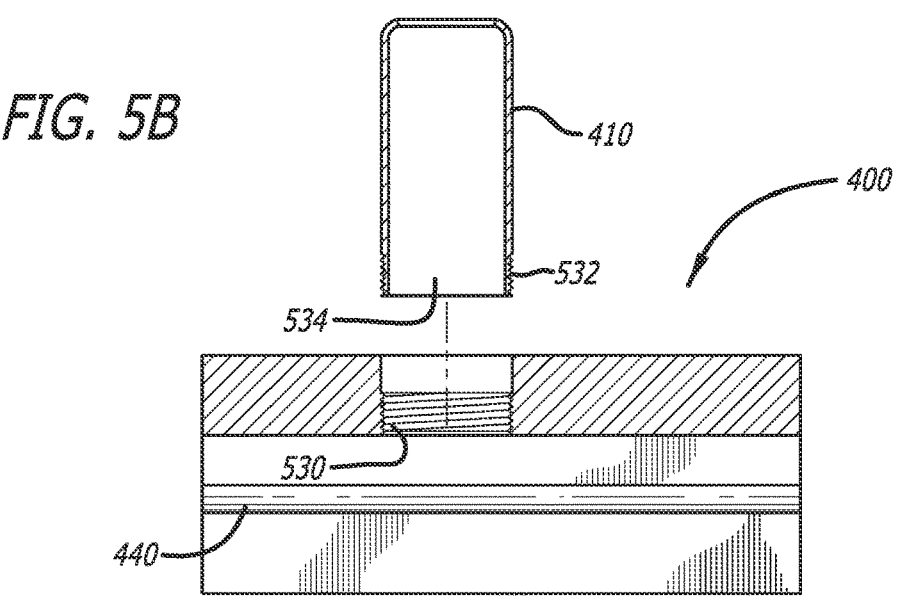

FIGS. 5A-5B illustrate alternative embodiments of vent adapters configured to couple with a collection container, according to some embodiments. In the illustration of FIGS. 5A-5B, the adapter 400 includes a cavity 412 and an aperture 414 formed in the cavity 412, and the port 410, where the port 410 is disconnected from the housing 420 of the adapter 400. Referring to FIG. 5A, the adapter 400 includes a ringed lip 510, and the port 410 includes an opening 520 having an exterior ridge 522. In the embodiment of FIG. 5A, the port 410 may be snapped into adapter 400 by placing the ridge 522 within the lip 510, to form a sealed interface for suctioning gas from a vent (e.g., with reference to FIG. 1A, the outlet vent 136). When port 410 is placed into ringed lip 510, a suction line may be attached to port 410 for transportation of gas.

Referring to FIG. 5B, the adapter 400 includes the aperture 414 having a threaded interior 530, and a port 410 that includes an opening 534 that includes threads 532. The threads 532 of the port 410 may be rotated into threaded opening 530 to form a sealed interface for suctioning gas from a vent (e.g., with reference to FIG. 1A, outlet vent 136). When the port 410 threadably coupled with the aperture 414, a suction line may be attached to the port 410 for transportation of gas.

Figure 5C:
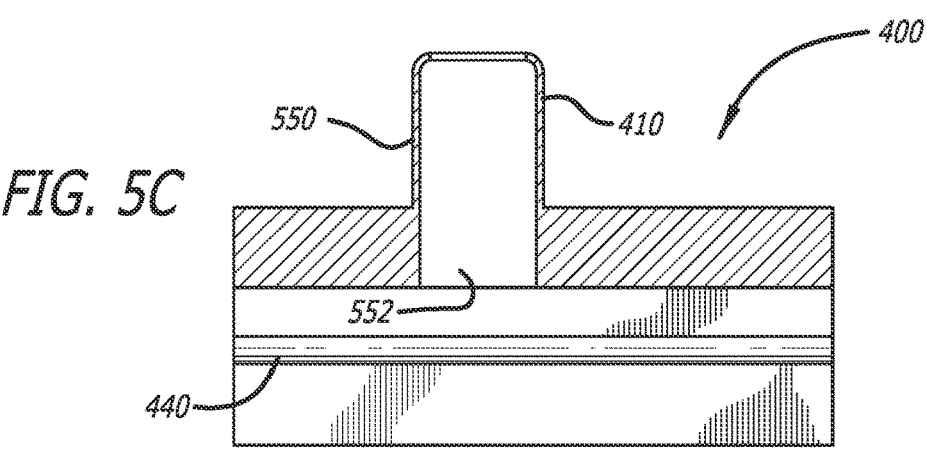

Referring now to FIG. 5C, a cross-section of an alternative embodiment of the adapter 400 is shown in accordance with some embodiments. The port 410 is illustrated as a one-piece extension of the adapter 400 with the aperture 552 providing a fluid passageway from the interior cavity 430 of the adapter 400 (see FIG. 3A) through the port 410. When the port 410 threadably coupled with the aperture 414, a suction line may be attached to the port 410 for transportation of gas.

While some particular embodiments have been disclosed herein, and while the particular embodiments have been disclosed in some detail, it is not the intention for the particular embodiments to limit the scope of the concepts provided herein. Additional adaptations and/or modifications can appear to those of ordinary skill in the art, and, in broader aspects, these adaptations and/or modifications are encompassed as well. Accordingly, departures may be made from the particular embodiments disclosed herein without departing from the scope of the concepts provided herein.

What is claimed is:

1. A lid adapter for coupling with a lid of a collection container, the lid including an outlet vent, comprising:
 a housing including a top surface and one or more side panels that are configured to couple with a top of the lid; and
 a port coupled to the top surface and configured to rotate between a first position and a second position, wherein when the lid adapter is coupled to the lid and the port is in the first position, a fluid seal is established between a distal end of the port and the top of the lid surrounding the outlet vent thereby enabling fluid flow from the outlet vent and through the port, wherein when the port is in the second position, the fluid seal is not established, and the outlet vent is in fluid communication with a surrounding environment.

2. The lid adapter of claim 1, wherein when the port is in the first position, the port is disposed perpendicularly to the top surface.

3. The lid adapter of claim 1, wherein the port is a hollow, cylindrical structure.

4. The lid adapter of claim 1, wherein a proximal end of the port is configured to couple with a suctioning airline.

5. The lid adapter of claim 1, wherein a rim of the distal end of the port includes an inward taper configured to create a suction effect resulting in the fluid seal.

6. The lid adapter of claim 1, wherein the one or more side panels extend perpendicularly from the top surface, and wherein an interior wall of each side panel includes a ridge configured to couple with a rim of the lid of the collection container.

7. The lid adapter of claim 1, wherein the port is coupled to the housing through a living hinge.

8. The lid adapter of claim 1, wherein the top surface includes a cavity having an aperture, and wherein when the port is in the first position, the distal end of the port is within the aperture of the cavity.

9. The lid adapter of claim 8, wherein the aperture includes a ringed lip and the distal end of the port includes a ridge, wherein when in the first position, the ridge engages the ringed lip.

10. The lid adapter of claim 8, wherein the aperture includes a threaded interior and the port includes a threaded exterior portion, wherein when in the first position, the port threadably couples with the aperture.

11. A fluid drainage system, comprising:
 a catheter;
 a collection container comprising a vent to allow gas to move into and out from the collection container;
 a drainage tube configured to urge a fluid from the catheter to the collection container;
 a gas suction line; and
 an adapter removably engaged with the collection container, the adapter comprising a port configured to couple with the gas suction line, the adapter rotatable between a first position and a second position, the port in the first position establishing a fluid seal and providing fluid communication between the gas suction line and the vent of the collection container, the port in the second position not establishing the fluid seal, wherein the vent is in fluid communication with a surrounding environment.

12. The fluid drainage system according to claim 11, wherein the vent of the collection container is an outlet vent configured to passively expel displaced air.

13. The fluid drainage system according to claim 11, wherein the adapter comprises a gap through which the port passes so as to couple with the vent of the collection container.

14. The fluid drainage system according to claim 11, wherein the collection container comprises a lid, wherein the vent of the collection container is positioned on the lid, and wherein the adapter is configured to couple with the vent by a sliding motion parallel to the lid.

15. The fluid drainage system according to claim 11, wherein the collection container is configured to collect the fluid comprising urine.

16. The fluid drainage system according to claim 11, wherein the collection container comprises a groove, and wherein the adapter comprises a ridge to couple with the groove.

17. The fluid drainage system according to claim 11, wherein the port in the first position is further configured to automatically lock around the vent in response to the adapter being attached to the vent by a sliding motion.

18. The fluid drainage system according to claim 11, wherein the collection container comprises a lid, wherein the vent is positioned on the lid, and wherein the adapter is configured to attach with the vent by a sliding motion at least substantially perpendicular to the lid.

19. The fluid drainage system according to claim 11, wherein the port in the first position is configured to seal around the vent of the collection container.

20. The fluid drainage system according to claim 11, wherein the port is configured to rotate in a circular direction from the second position to the first position to seal around the vent.

21. The fluid drainage system according to claim 11, wherein the port of the adapter is configured to seal around the vent by at least one of a rotation into the first position; a torsional rotation; a snap fit connection; or a living hinge.

22. The fluid drainage system according to claim 11, wherein an axis of the port in the first position aligns parallel with an axis of the vent, and wherein the axis of the port in the second position extends perpendicular to the axis of the vent.

* * * * *